(12) United States Patent
Khademhosseini

(10) Patent No.: US 10,813,792 B2
(45) Date of Patent: Oct. 27, 2020

(54) SYSTEM AND METHOD FOR REMOVAL OF EARWAX AND PARTICULATES

(71) Applicant: ND Products Inc., Falls Church, VA (US)

(72) Inventor: Nami Khademhosseini, Falls Church, VA (US)

(73) Assignee: ND PRODUCTS INC., Falls Church, VA (US)

( * ) Notice: Subject to any disclaimer, the term of this patent is extended or adjusted under 35 U.S.C. 154(b) by 1195 days.

(21) Appl. No.: 14/737,511

(22) Filed: Jun. 12, 2015

(65) Prior Publication Data
US 2016/0361203 A1    Dec. 15, 2016

(51) Int. Cl.
| | | |
|---|---|---|
| *A61F 11/00* | (2006.01) | |
| *A61M 1/00* | (2006.01) | |
| *A61F 13/38* | (2006.01) | |
| *A61M 3/00* | (2006.01) | |
| *A61M 3/02* | (2006.01) | |

(52) U.S. Cl.
CPC ............ *A61F 11/006* (2013.01); *A61F 13/38* (2013.01); *A61M 1/0058* (2013.01); *A61M 1/0084* (2013.01); *A61M 3/005* (2013.01); *A61M 3/0262* (2013.01); *A61M 3/0279* (2013.01); *A61M 1/0072* (2014.02); *A61M 2210/0662* (2013.01)

(58) Field of Classification Search
CPC .................. A61F 11/006; A61F 13/38; A61M 2210/0662; A61M 2210/0668; A61M 2210/0675
See application file for complete search history.

(56) References Cited

U.S. PATENT DOCUMENTS

| | | | | |
|---|---|---|---|---|
| 1,980,826 | A | * | 11/1934 | Reiss .................... A61F 11/006 15/209.1 |
| 2,170,222 | A | * | 8/1939 | Strauss .................... A61F 13/38 604/2 |
| 4,746,238 | A | | 5/1988 | Levine |
| 5,107,861 | A | | 4/1992 | Narboni |
| 5,456,265 | A | * | 10/1995 | Yim .................... A61B 10/0291 600/569 |
| 5,509,921 | A | * | 4/1996 | Karell .................... A61B 1/227 606/162 |
| 5,593,402 | A | * | 1/1997 | Patrick .................... A61B 17/29 604/902 |
| 5,715,850 | A | * | 2/1998 | Markgraaf ............ A61F 11/006 132/333 |
| 5,888,199 | A | * | 3/1999 | Karell ................... A61F 11/006 606/162 |

(Continued)

*Primary Examiner* — Alexander J Orkin
(74) *Attorney, Agent, or Firm* — Aslan Law, P.C.

(57) ABSTRACT

In one example, we describe a method and apparatus for cleaning the ear canal of cerumen contaminants, dust, and particulates. That includes a handle and replaceable tips, a combination of a flared design and solid base plate attached to the bottom of the tips, limiting the excessive insertion of the tip into the deep area of ear canal that could contact eardrum, which can seriously damage the eardrum and hearing capabilities. The handle has a slot in the front in which a tip can snap into, and as the whole system is secured together, the user can operate the system by spinning the handle, using fingers, e.g., in a clockwise direction, as the user proceeds to insert the tip in the ear canal. Different variations are also presented here.

19 Claims, 42 Drawing Sheets

(56) References Cited

U.S. PATENT DOCUMENTS

| | | | |
|---|---|---|---|
| 5,982,908 A | 11/1999 | Bauman | |
| 6,152,940 A * | 11/2000 | Carter | A61F 11/006 604/97.02 |
| 6,695,802 B1 * | 2/2004 | Thompson | A61F 11/006 604/1 |
| 6,706,023 B1 * | 3/2004 | Huttner | A61M 3/0283 604/264 |
| 7,074,230 B2 | 7/2006 | Olson | |
| D545,431 S | 6/2007 | Khademhosseini | |
| 7,658,745 B2 | 2/2010 | Olson | |
| D701,600 S | 3/2014 | Kauffman | |
| 8,777,972 B2 | 7/2014 | Burres | |
| 2003/0181933 A1 * | 9/2003 | Eicoff | A61F 13/38 606/162 |
| 2003/0187469 A1 * | 10/2003 | Olson | A61F 11/006 606/162 |
| 2004/0097997 A1 * | 5/2004 | Di Cecco | A61F 11/006 606/162 |
| 2006/0085018 A1 * | 4/2006 | Clevenger | A61F 11/006 606/162 |
| 2008/0142385 A1 | 6/2008 | Stein et al. | |
| 2008/0300527 A1 * | 12/2008 | Bivins | A61F 13/38 604/1 |
| 2009/0012424 A1 * | 1/2009 | Huschmand Nia | A61B 10/0045 600/569 |
| 2011/0066172 A1 * | 3/2011 | Silverstein | A61F 11/006 606/162 |
| 2011/0301572 A1 * | 12/2011 | Vlodaver | A61F 11/00 604/514 |
| 2012/0296355 A1 * | 11/2012 | Burres | A61F 11/006 606/162 |
| 2013/0190647 A1 * | 7/2013 | Pahuja | A61B 5/1076 600/559 |
| 2015/0142029 A1 | 5/2015 | Fahn et al. | |

* cited by examiner

120

122

124

122

140

142

154

164

166

170

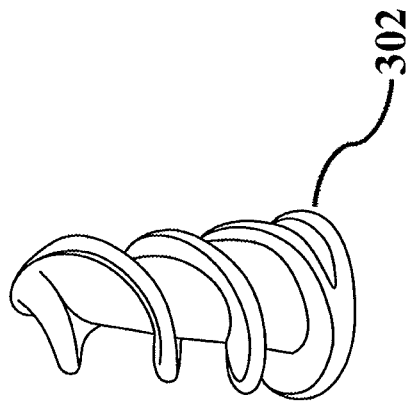
FIG. 30A
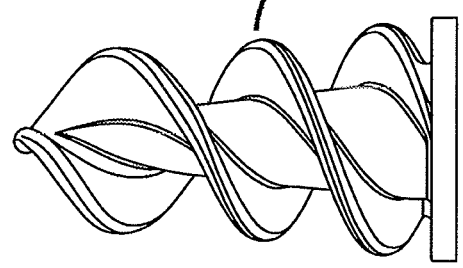
FIG. 30C
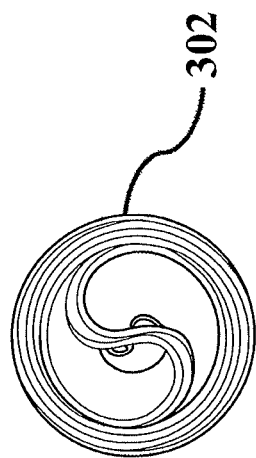
FIG. 30B
FIG. 30D
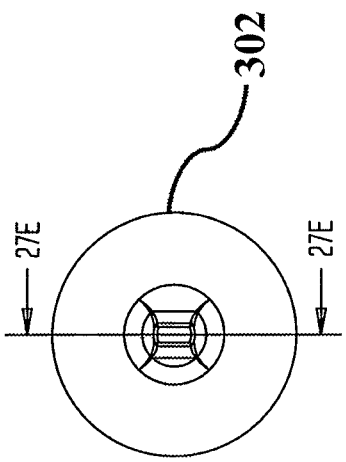
FIG. 30E
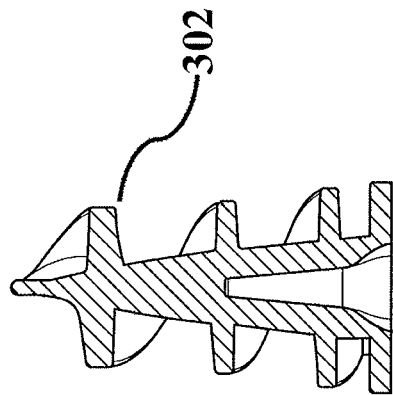
FIG. 30G
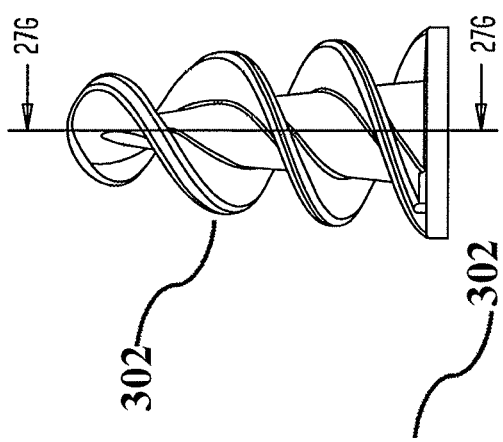
FIG. 30F

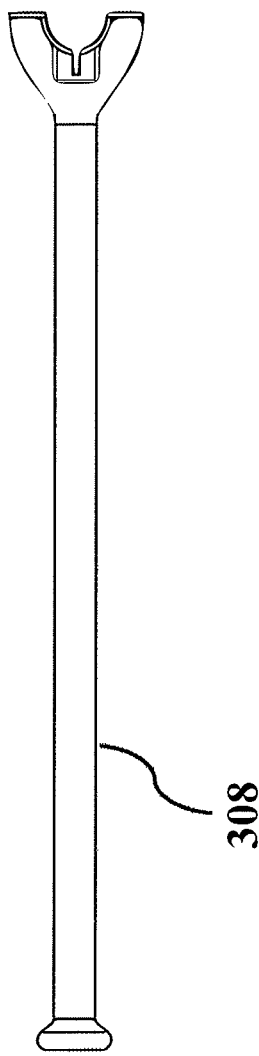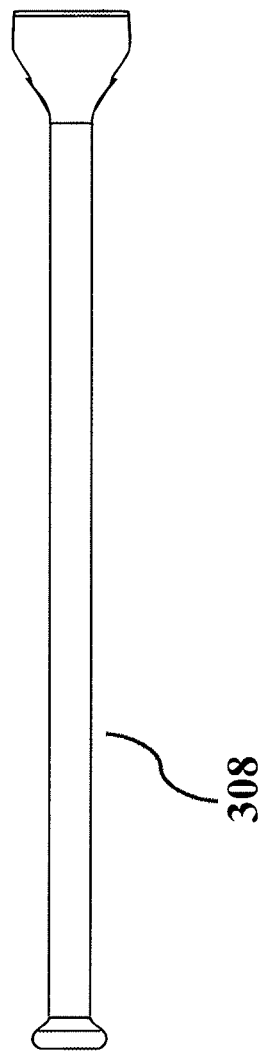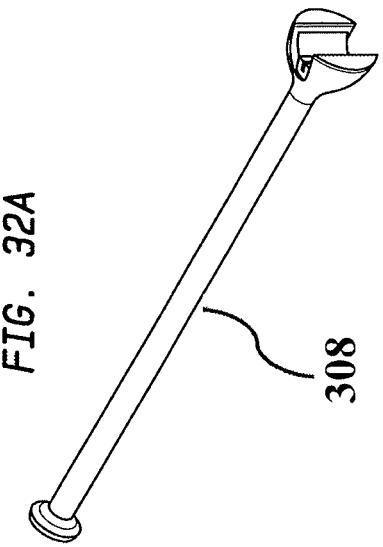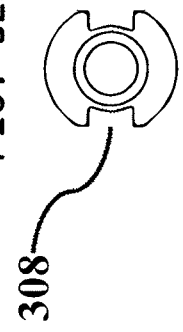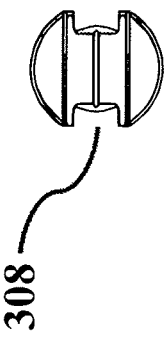

SYSTEM AND METHOD FOR REMOVAL OF EARWAX AND PARTICULATES

BACKGROUND OF THE INVENTION

The ear canal in human produce cerumen, also known as "earwax", in outer part of the ear canal. The use of audio and mobile device's ear buds, hearing aid buds, or sound protector ear plugs can push the earwax deeper into the ear canal, in which case it can cause many complications, such as reduction of hearing, due to earwax plague in the ear canal. Cerumen Impaction (Earwax Buildup and Blockage) is a major problem for many people. Regular Q-tip or cotton swab usually push the earwax further in, blocking and possibly damaging the ear.

This invention solves this problem, by using a system to remove ear wax properly. However, the invention and embodiments described here, below, have not been addressed or presented in any prior art. For example, some other patents are: D545431 by N. Khademhosseini, PN 8,777,972 by Steven Burres (Device and method for removing earwax), 6,695,802 (Ear cleaner device), 5,982,908 (Ear wax collection device for a hearing aid), and 5,107,861 (Safe ear clean button and protection with attachment device).

SUMMARY OF THE INVENTION

In one embodiment, we describe a method and a device for cleaning the ear canal of cerumen contaminants, dust, and particulates. That includes a handle and replaceable tips, a combination of a flared design and solid base plate attached to the bottom of the tips, limiting the excessive insertion of the tip into the deep area of ear canal that could contact eardrum, which can seriously damage the eardrum and hearing capabilities.

The handle has a slot in the front in which a tip can snap into, and as the whole system is secured together, the user can operate the system by spinning the handle, using fingers, in a clockwise direction, as the user proceeds to insert the tip in the ear canal. The handle also can be made, as a new design for syringe, to hold and dispense liquid that may facilitate the ear cleansing in different type of ear with different earwax condition.

BRIEF DESCRIPTION OF THE DRAWINGS

FIG. 30A is for one embodiment, as an example, for tip.
FIG. 30B is for one embodiment, as an example, for tip.
FIG. 30C is for one embodiment, as an example, for tip.
FIG. 30D is for one embodiment, as an example, for tip.
FIG. 30E is for one embodiment, as an example, for tip.
FIG. 30F is for one embodiment, as an example, for tip.
FIG. 30G is for one embodiment, as an example, for tip.
FIG. 32A is for one embodiment, as an example, for handle.
FIG. 32B is for one embodiment, as an example, for handle.
FIG. 32C is for one embodiment, as an example, for handle.
FIG. 32D is for one embodiment, as an example, for handle.
FIG. 32E is for one embodiment, as an example, for handle.

DETAILED DESCRIPTION OF THE PREFERRED EMBODIMENTS

Figure 1:
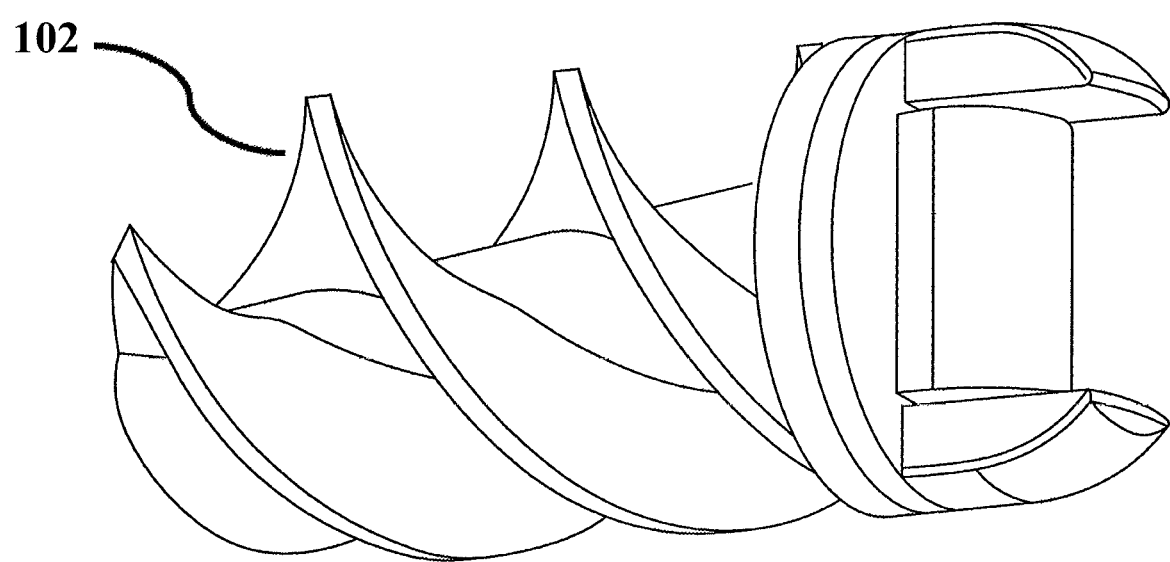
FIG. 1 is for one embodiment, as an example, for tip.

The invention enables a user to perform a proper ear cleaning at home and without the need of visiting a doctor for ear cleaning. One embodiment features a flared design, combined with solid plate at the tip base, limiting penetration into ear canal, therefore, preventing it from reaching to eardrum, to prevent injury.

One embodiment features:

Soft spirally finned tip that excavate and exfoliate earwax and articulates outward, and prevent pushing it further.
A handle locking system, specifically designed to:
  i. snap into the back of the tip, to work as a system for spinning the spiral tip.
  ii. It comprises of locking tabs that can be pushed forward by the user (after use) to snap off the tip, to facilitate disposal of the used tip, without the need of touching them, for cleanliness and better hygiene.
  iii. Handle adapted to be grabbed by hand, and it can be made in two different categories for two separate methods of use:
    1. a solid piece, just as handle.
    2. a hollow handle that comprises of a syringe system to load, store, dispense, or spray a liquid into the ear canal, either
      before installing a tip to handle, or with open cell tip on it (opening in the foam, to allow liquid through the tip, around the ear canal). In this case, there will be an opening within the core piece that connects the tip to the handle to direct the liquid from handle to the tip.

Please refer to the 3D CAD design files in FIGS. 1 to 45 for some embodiments and variations, with details.

One embodiment is a handle which comprises of a syringe system. The end of the handle is connected to the short piston (about half size of the handle's length), which can unlock from the body of the handle by a twist, so it can be free to be pulled back and out, which results to vacuuming function that pulls liquid in.

One embodiment is a tip that comprises of an opening in the middle of the bottom of the tip core piece, which directs liquid from handle to the tip.

One embodiment is a core locking piece with opening that allows liquid inside the handle to be sprayed in different angles inside the ear canal, before a tip is added to the system. In this method, consumer sprays wash inside ear directly with the liquid. After softening some hard earwax, one applies the tip on top of the sprayer to swab inside the ear canal and also to get the moist out.

One embodiment is a handle that comprises of a squeezable syringe bulb at the front flared part of the handle.

One embodiment is a handle, comprising of a squeezable syringe bulb at the end of the handle which helps the handle to work like a dripper. After spray wash inside ear, a tip can be snapped on the front of the handle, in order to spin the spiral tip for cleaning and getting the moistout.

Please note the importance of the flared design of the tip and the round plate at bottom (works as a stopper), that discourages the excessive penetration of the tip into the ear canal which results in safeguarding ear drum from accidental perforation.

Figure 2:
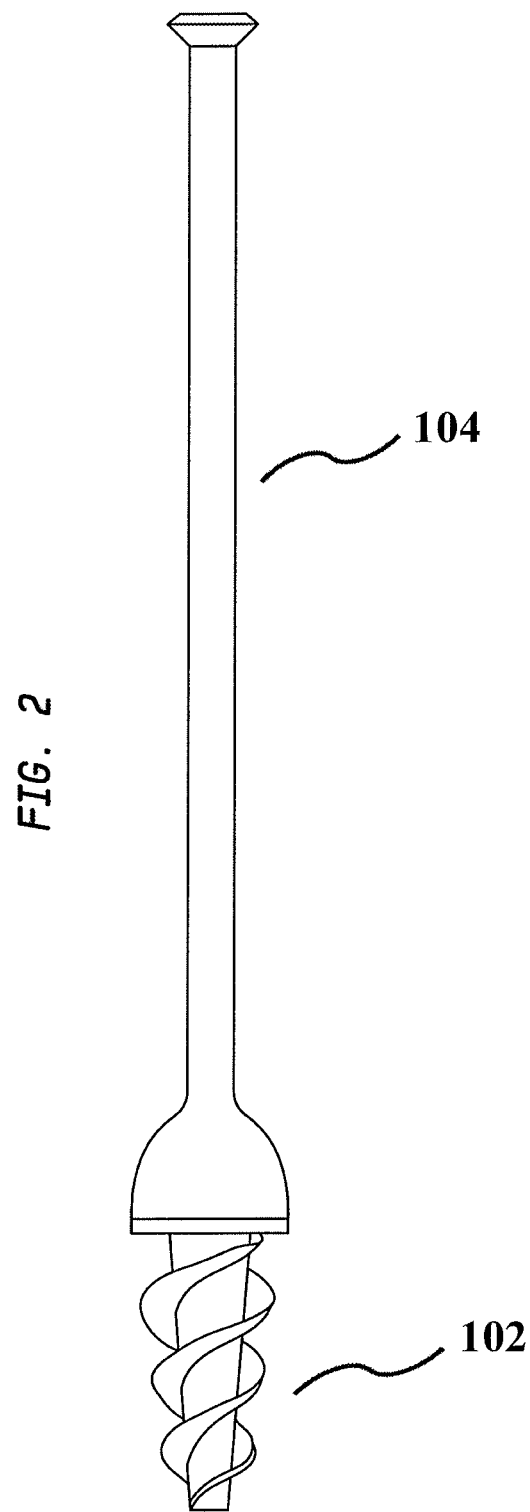
FIG. 2 is for one embodiment, as an example, for handle and tip.
Figure 3:
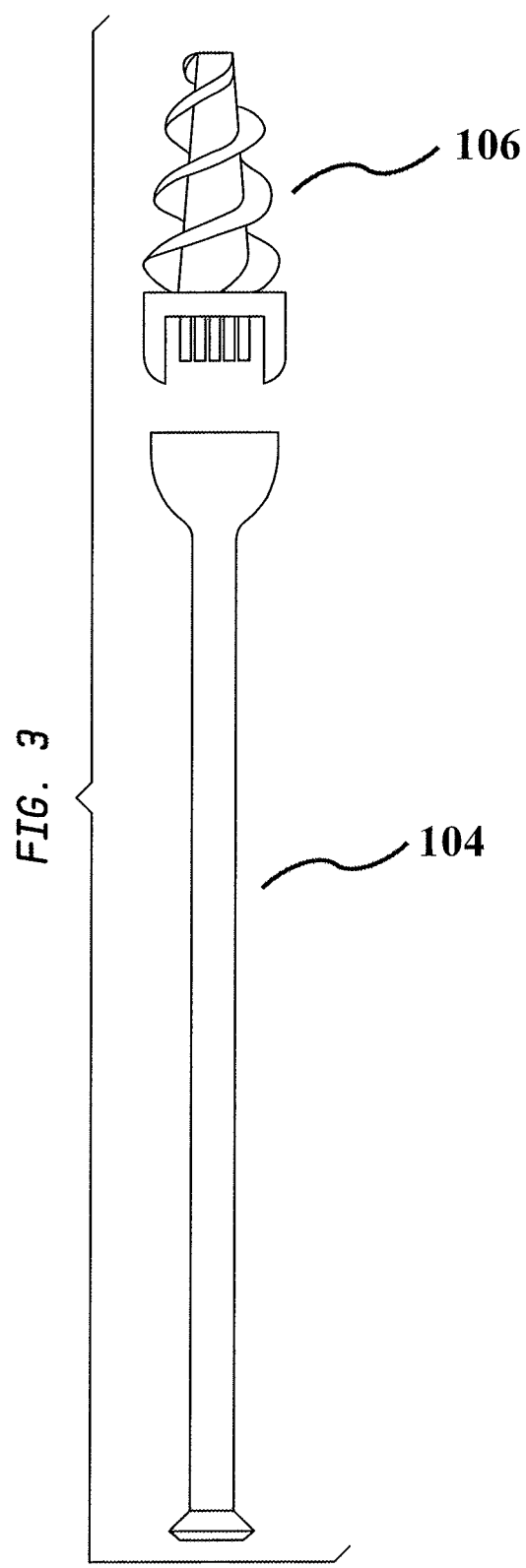
FIG. 3 is for one embodiment, as an example, for handle and tip.
Figure 4:
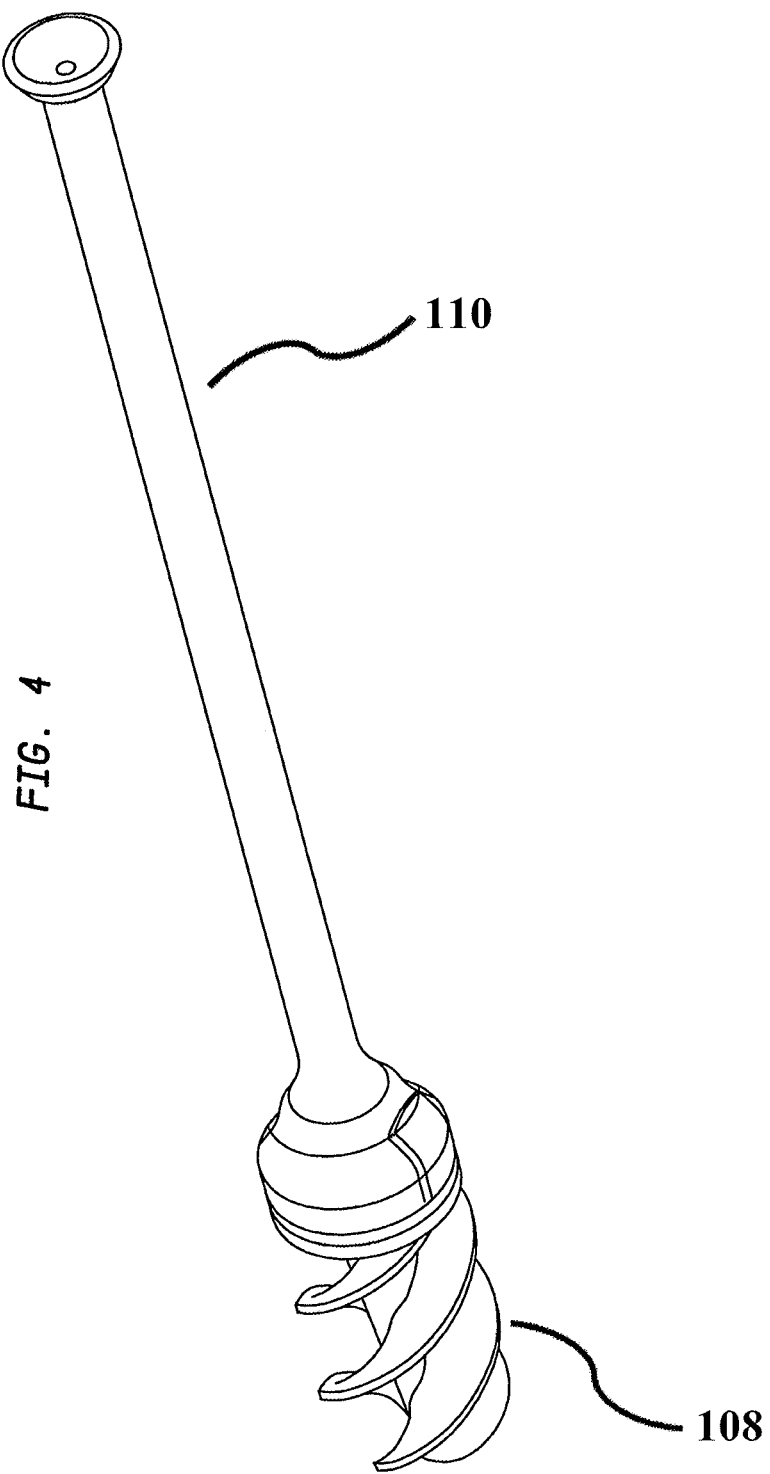
FIG. 4 is for one embodiment, as an example, for handle and tip.
Figure 5:
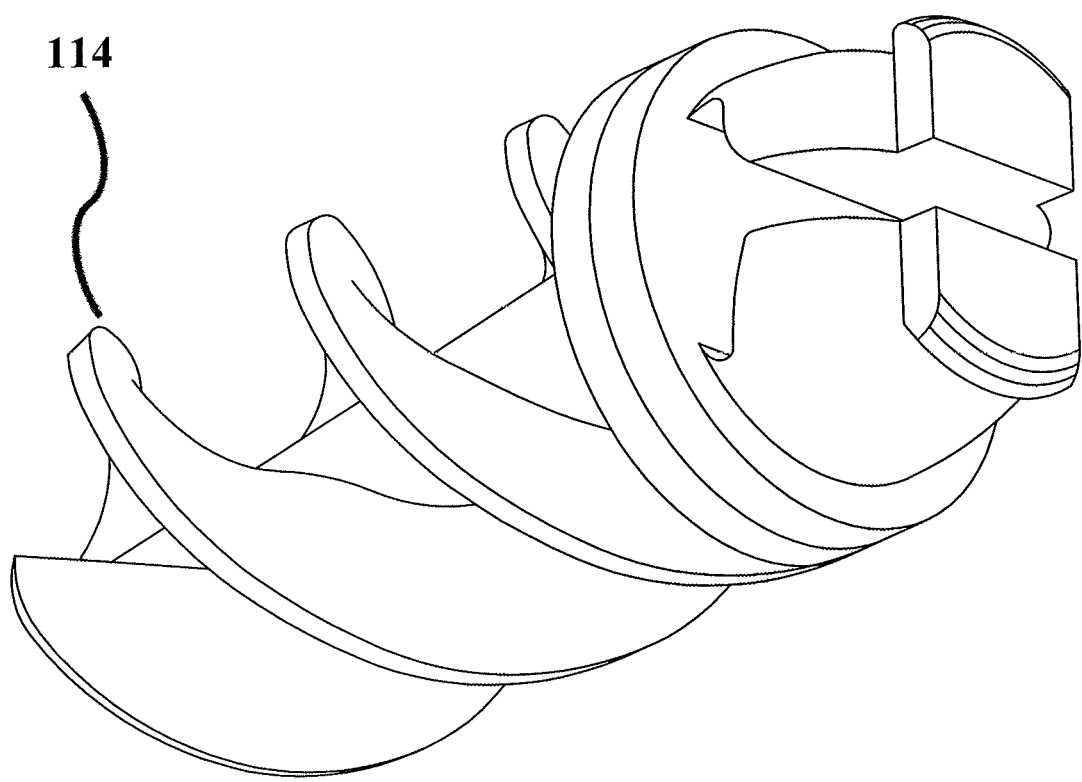
FIG. 5 is for one embodiment, as an example, for tip.
Figure 6:
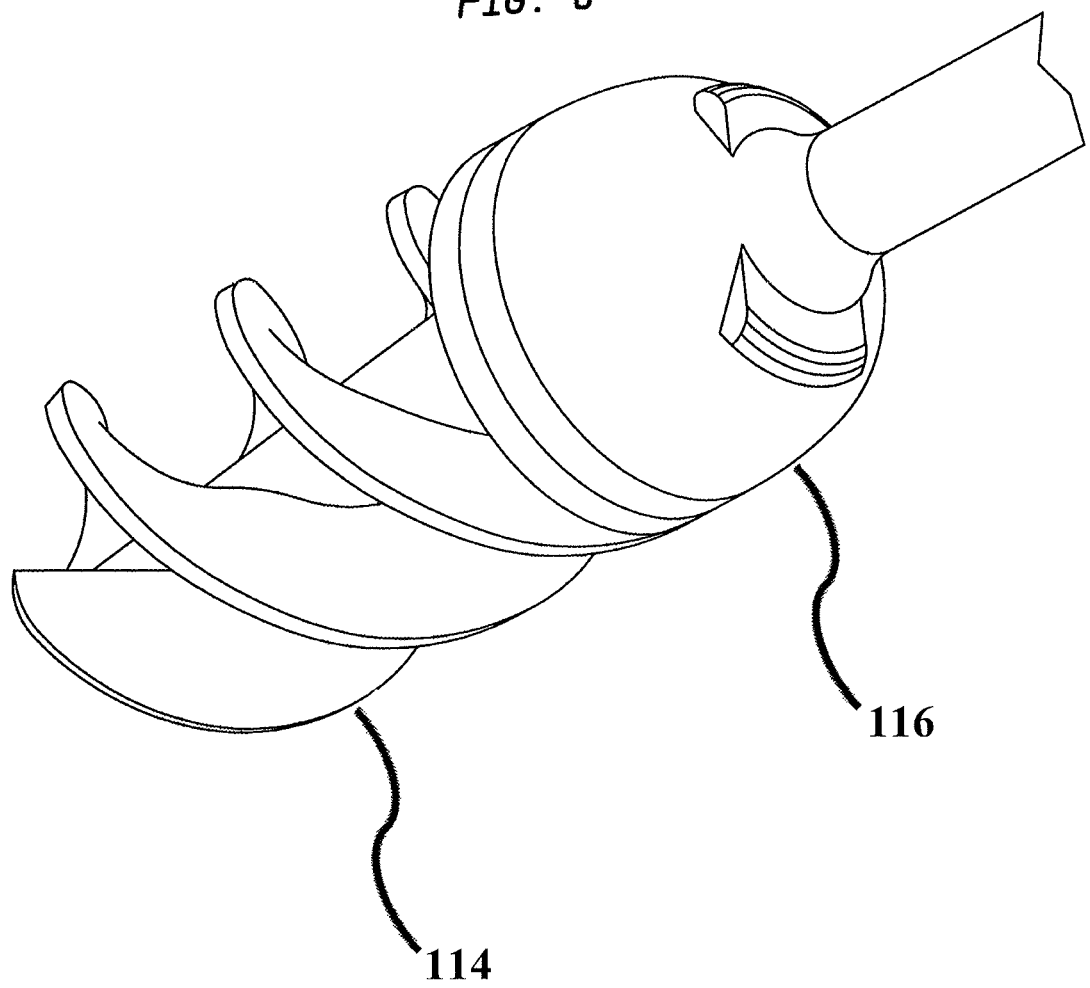
FIG. 6 is for one embodiment, as an example, for tip and handle.
Figure 7:
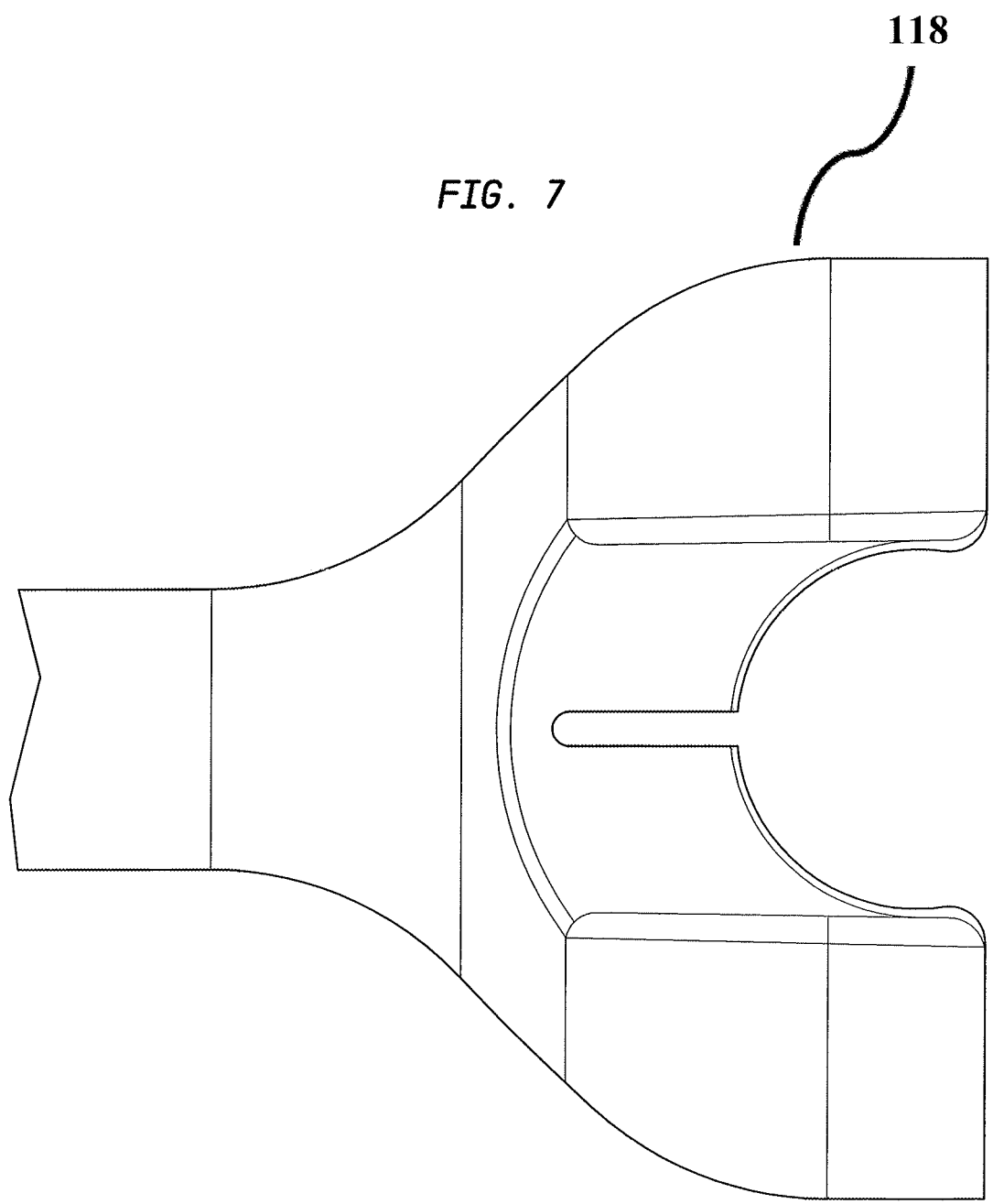
FIG. 7 is for one embodiment, as an example, for handle.

FIG. 1 shows a. 3-D view of the tip 102, for one embodiment. FIG. 2 shows a 3-D view of the tip 102 and handle 106, together, as one piece, for one embodiment. FIG. 3 shows a 3-D view of the tip 106 and handle 104, separated, as 2 pieces, for one embodiment. FIG. 4 shows a 3-D view of the tip 108 and handle 110, together, as one piece, attached, for one embodiment. FIG. 5 shows a 3-D view of the tip 112, for one embodiment. FIG. 6 shows a 3-D view of the tip 114, attached to a handle 116, for one embodiment. FIG. 7 shows a 3-D view of the connection mechanism 118 between tip and handle, for one embodiment.

FIGS. 30A to 30G show 3-D views of the tip 302, from various angles and cross sections, with dimensions for a typical example, for one embodiment. FIGS. 31A to 31E show 3-D views of the core 304 and connection mechanism 306, from various angles and cross sections, with dimensions for a typical example, for one embodiment. FIGS. 32A to 32E show 3-D views of the handle 308, from various angles and cross sections, with dimensions for a typical example, for one embodiment.

Figure 8:
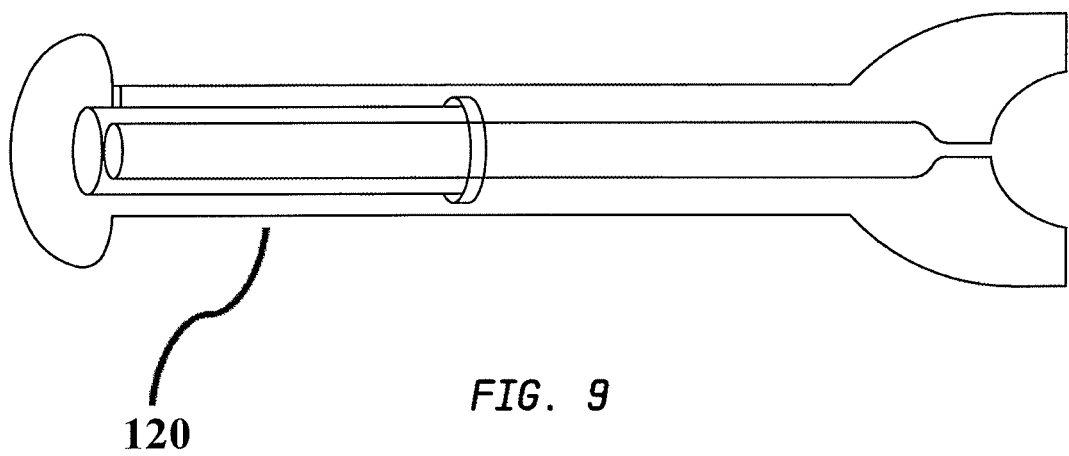
FIG. 8 is for one embodiment, as an example, for handle.
Figure 9:
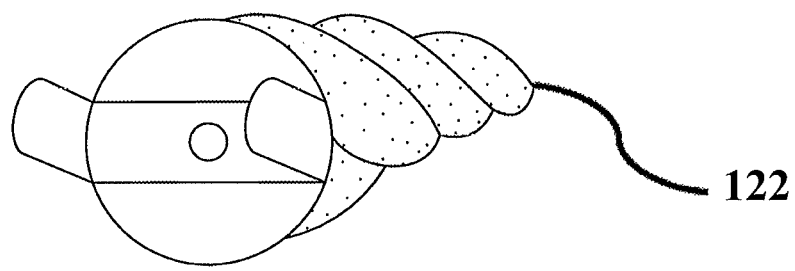
FIG. 9 is for one embodiment, as an example, for tip
Figure 10:
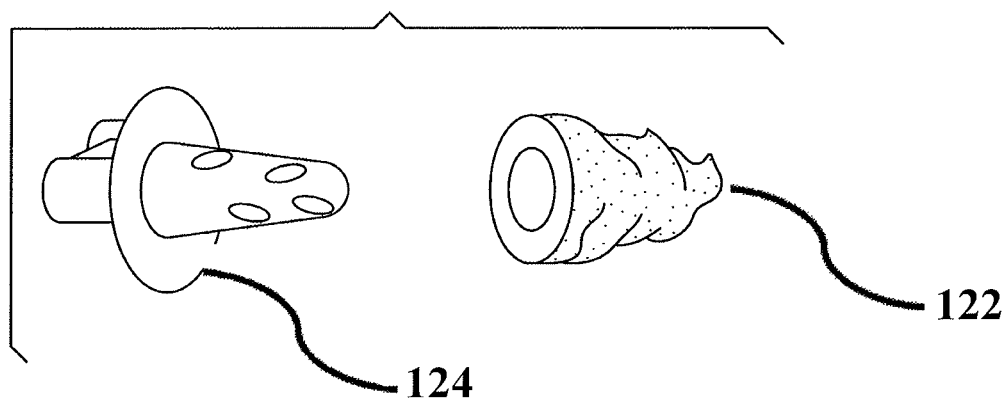
FIG. 10 is for one embodiment, as an example, for tip.
Figure 11:
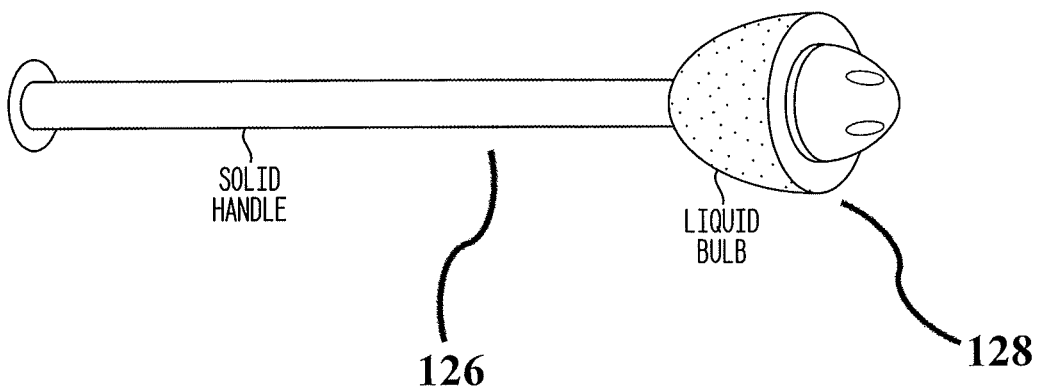
FIG. 11 is for one embodiment, as an example, for handle and liquid bulb.

FIG. 8 shows a view of the body 120 with container in the middle, for one embodiment. FIG. 9 shows a view of the tip 122, for one embodiment. FIG. 10 shows a view of the tip 122 with matching ending 124, with holes, for one embodiment. FIG. 11 shows a view of the solid handle 126 with liquid bulb 128, with holes, for suction of liquid, for one embodiment, for cleaning, rinsing, flushing, soaking, dissolving, medicating, drug-delivery, coating, or drying (the ear or the wax or the dirt). The soft plastic or elastic bulb or rubber can be pushed in by fingers, and then get back to the original spherical shape by itself, to suck the air or liquid or fluid from the ear or container or bottle or jar, for any or all the purposes mentioned above.

Figure 12:
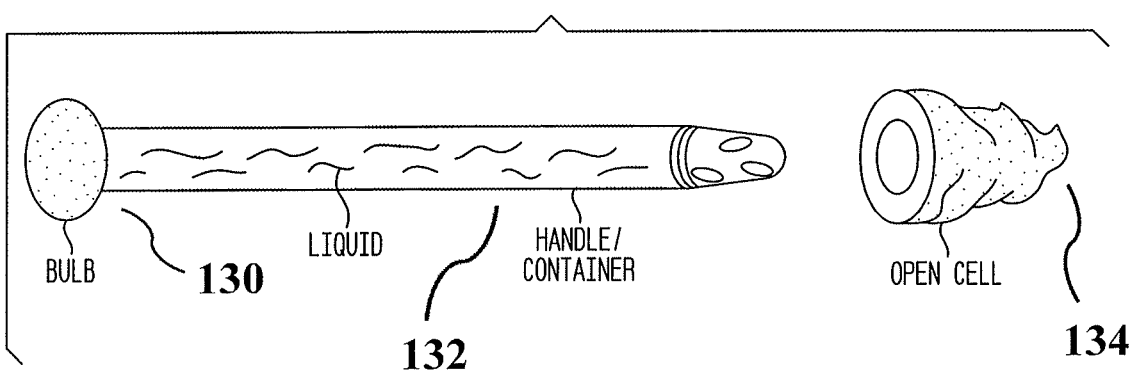
FIG. 12 is for one embodiment, as an example, for handle and tip.

FIG. 12 shows a bulb 130 at the end of the handle 132, doing the same function as described above, with container within or hollow body, to have the liquid or fluid in, for storage and later usage, in the long handle, with tip 134 narrowing down, with holes near the tip of the handle 132, which will match and inserted into an open cell foam tip 134 or other tips (e.g., replaceable or exchangeable or temporary or disposable or permanent tip, with different materials or properties), as shown in the figure, for one embodiment.

Figure 13:
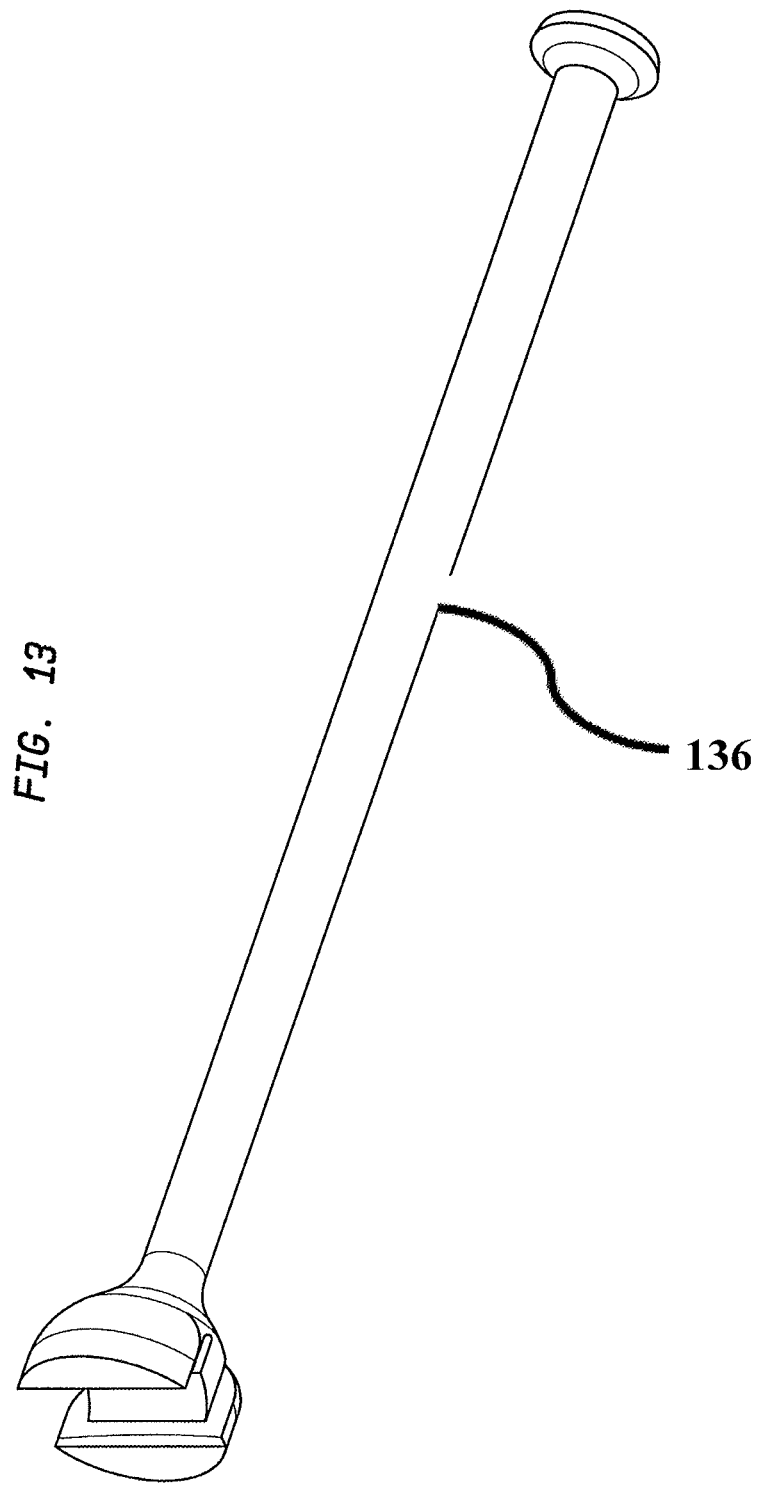
FIG. 13 is for one embodiment, as an example, for handle.

FIG. 13 shows a view of the body, with handle 136, for one embodiment. One end is circular flat for holding fingers or as marker, and the other end is for engaging and attaching to the tip.

Figure 14:
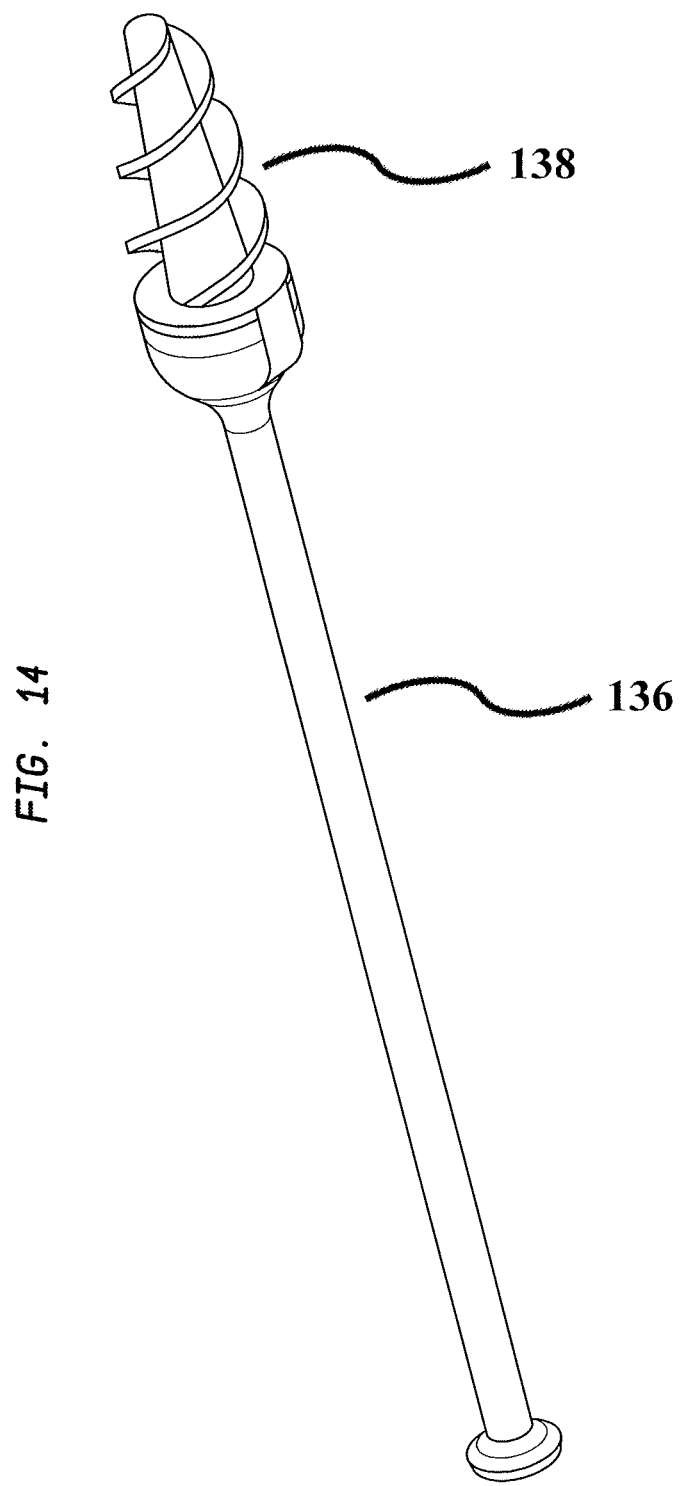
FIG. 14 is for one embodiment, as an example, for handle and tip.
Figure 15:
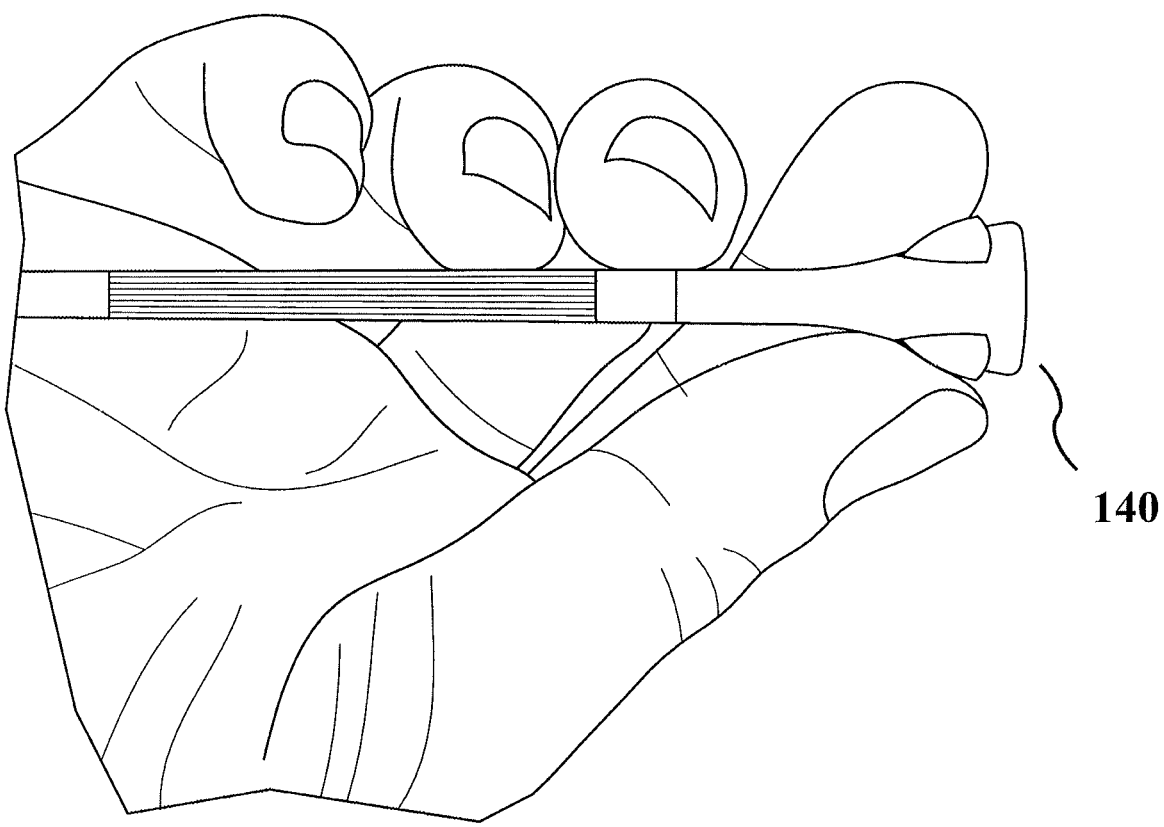
FIG. 15 is for one embodiment, as an example, for handle.
Figure 16:
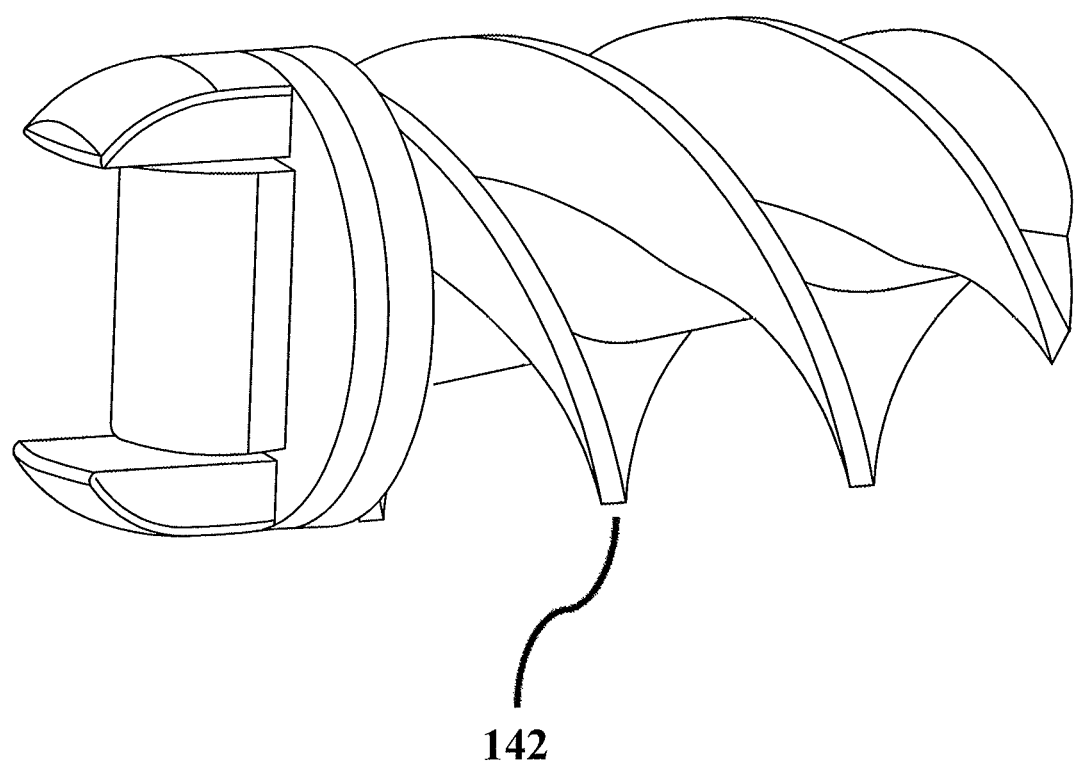
FIG. 16 is for one embodiment, as an example, for tip.
Figure 17:
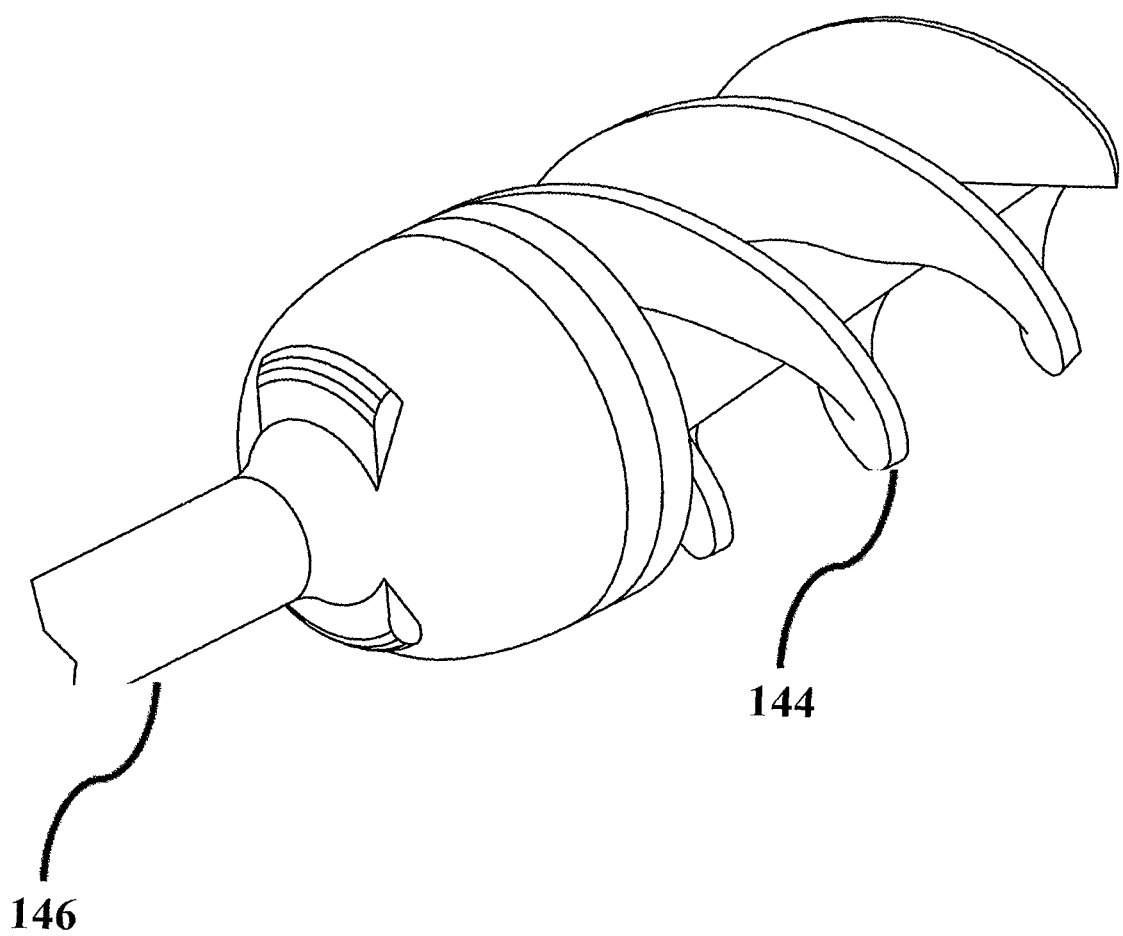
FIG. 17 is for one embodiment, as an example, for handle and tip.

FIG. 14 shows a view of the body, with handle 136, with spiral tip 138 attached on one end, for one embodiment. FIG. 15 shows a view of the body, with handle 140, at one end, for one embodiment. FIG. 16 shows a view of the tip, with spiral tip 142, with attaching or engaging end, for one embodiment. FIG. 17 shows a view of the tip, with spiral tip 144, attached to a body 146, for one embodiment.

Figure 18:
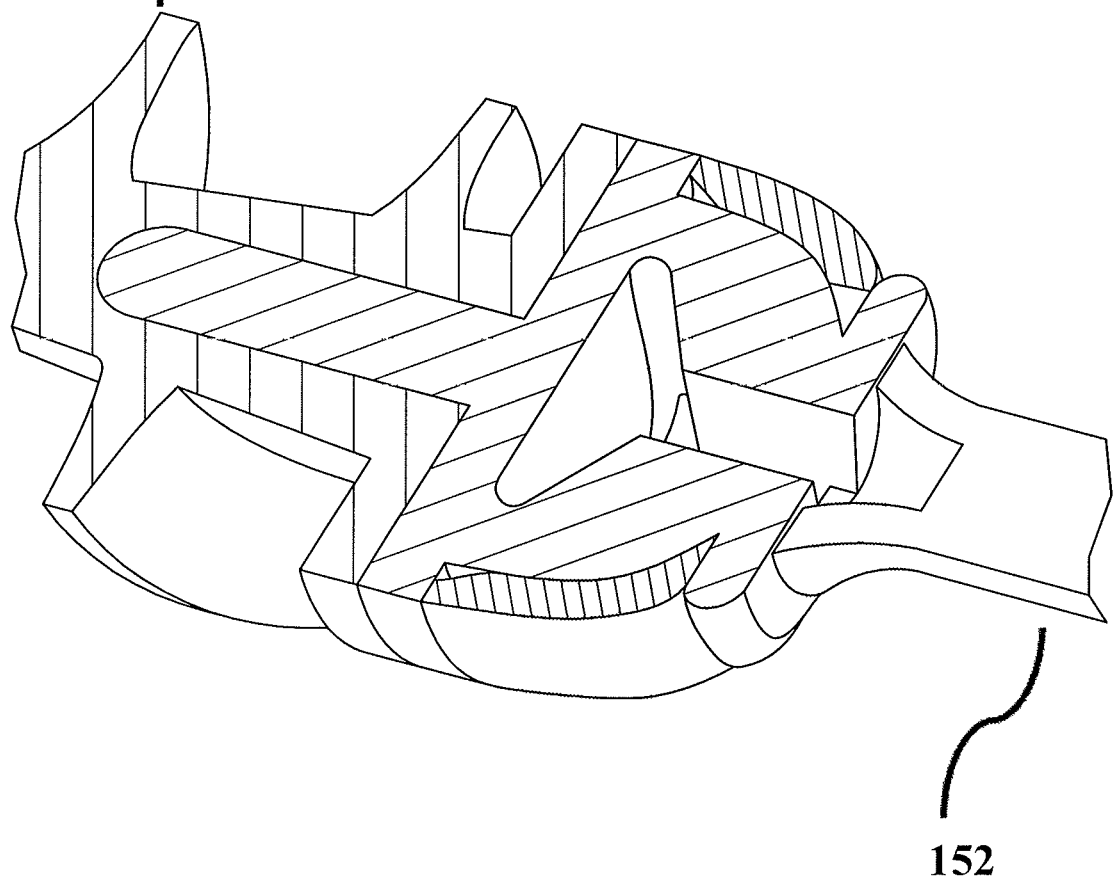
FIG. 18 is for one embodiment, as an example, for tip.
Figure 19:
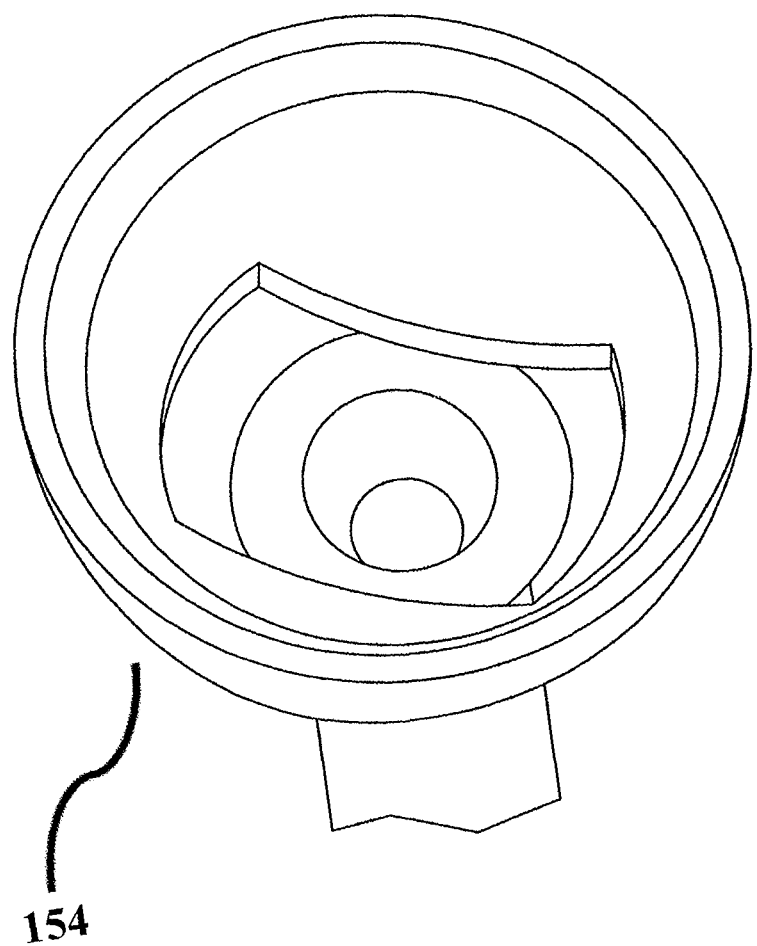
FIG. 19 is for one embodiment, as an example, for handle.

FIG. 18 shows a view of the tip, with spiral tip 150, attached to a body 152, for one embodiment, shown as a cross section, cut in half, along the length. FIG. 19 shows a view of the body 154, at one end, for attachment to a tip, with gaps or slits or cuts or openings, to engage the tip and attach to the tip, for one embodiment.

Figure 20:
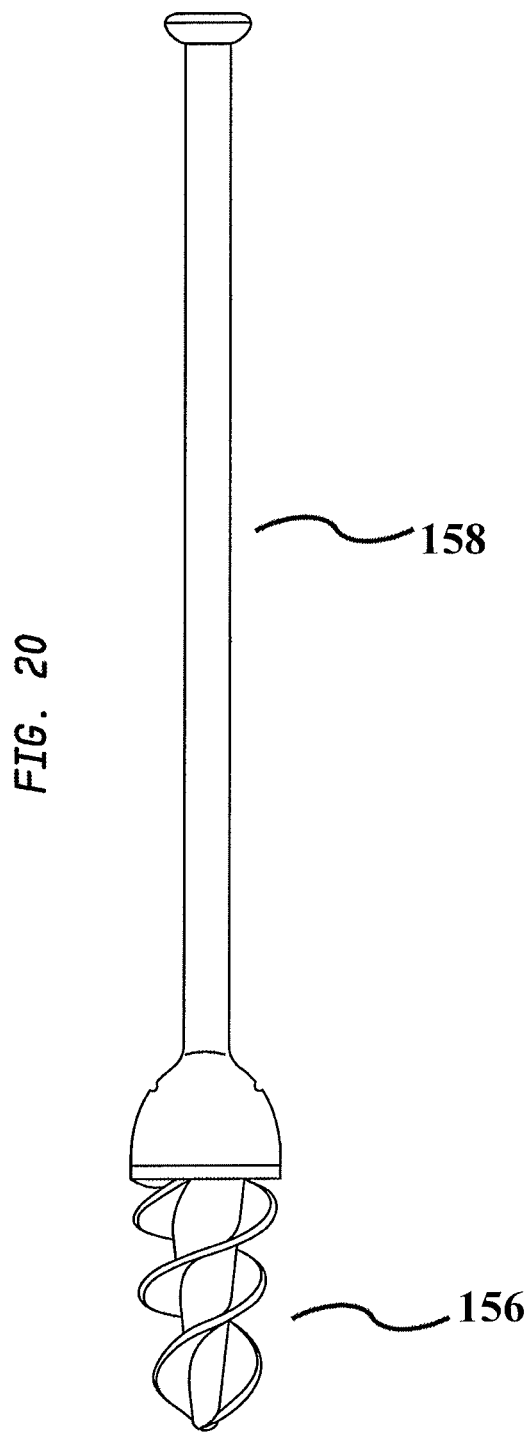
FIG. 20 is for one embodiment, as an example, for handle and tip.
Figure 21:
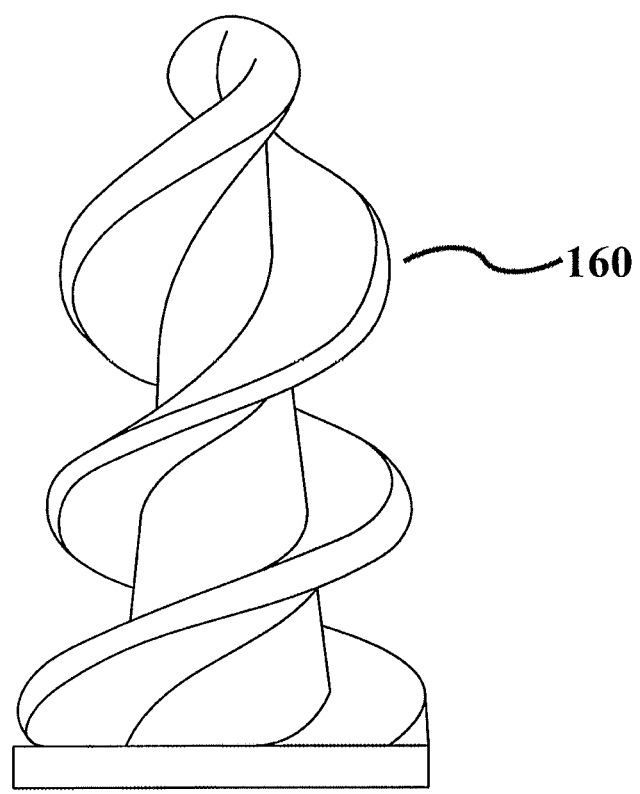
FIG. 21 is for one embodiment, as an example, for tip.
Figure 22:
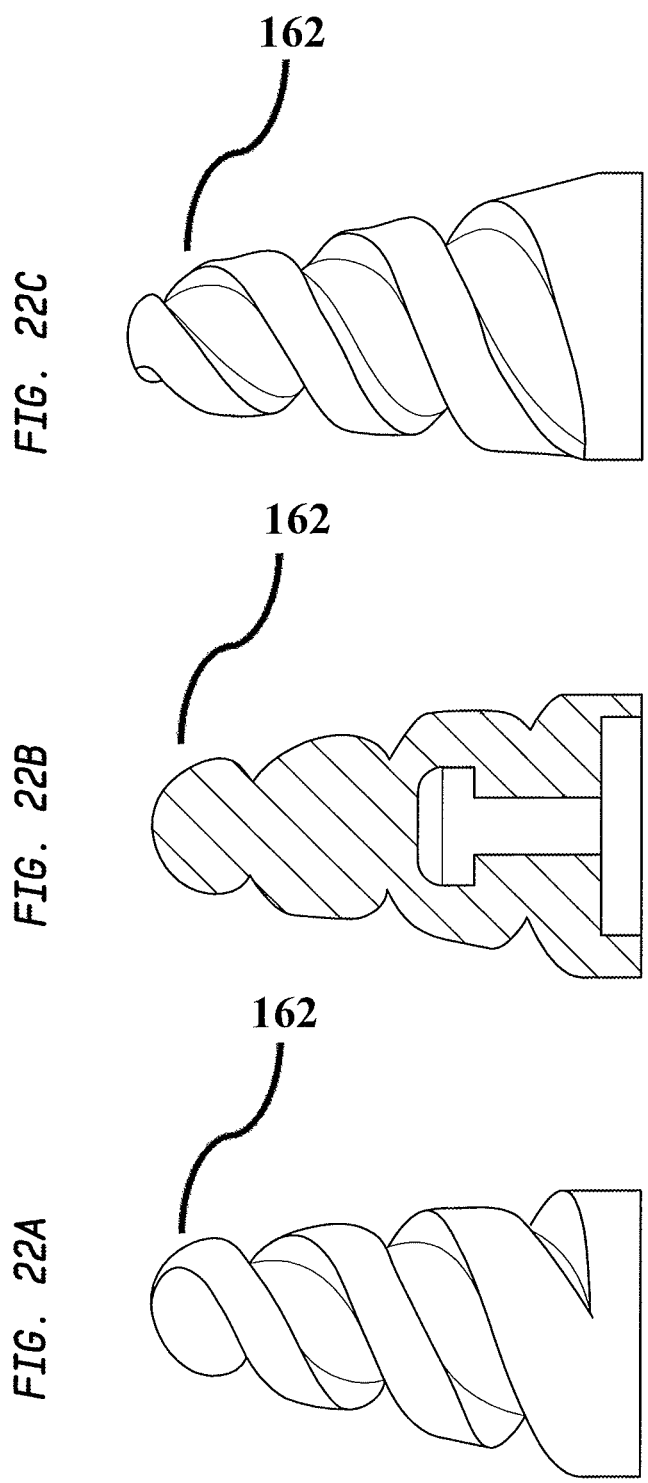
FIG. 22A is for one embodiment, as an example, for tip.
FIG. 22B is for one embodiment, as an example, for tip.
FIG. 22C is for one embodiment, as an example, for tip.

FIG. 20 shows a view of the tip, with spiral tip 156, attached to a body 158, for one embodiment. FIG. 21 shows a view of the tip, with spiral tip 160, for one embodiment.

Figure 23:
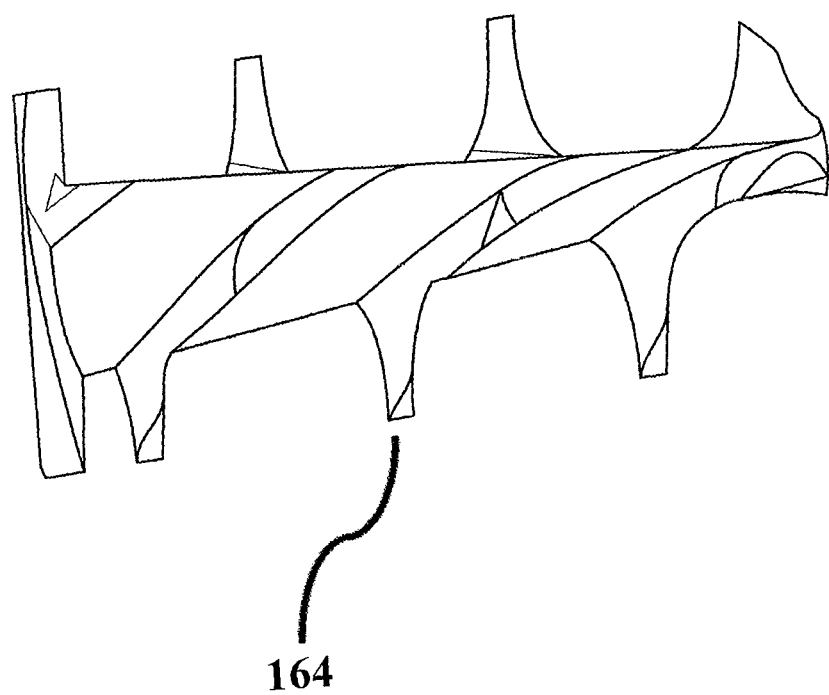
FIG. 23 is for one embodiment, as an example for tip.
Figure 24:
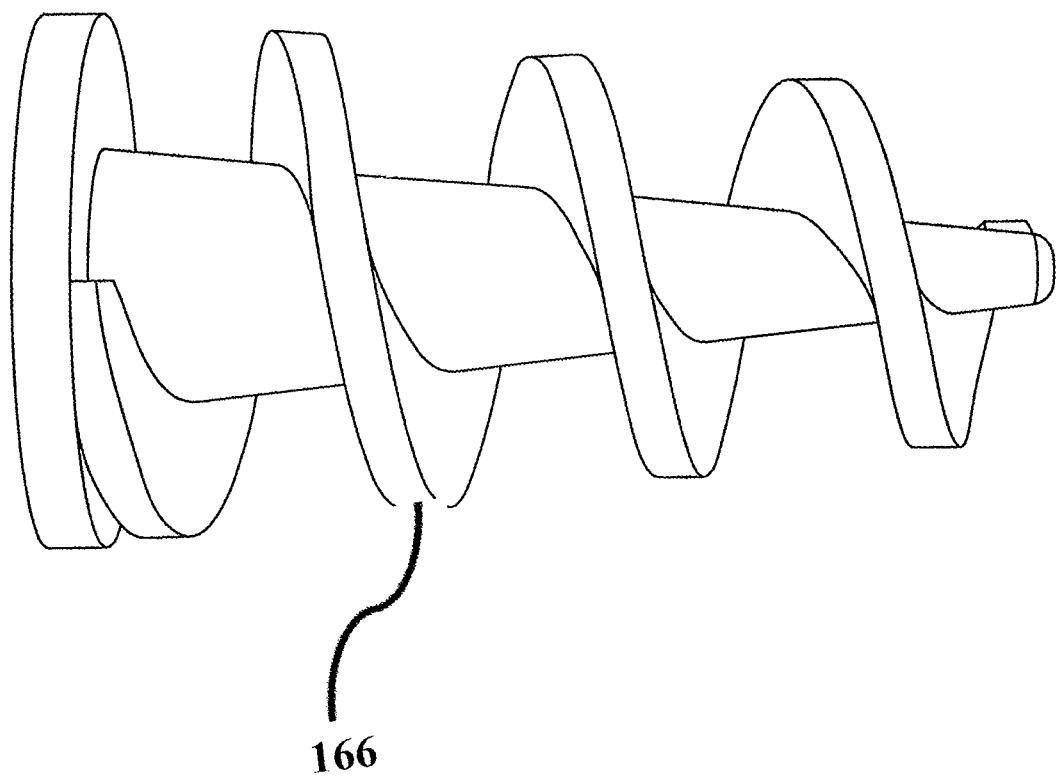
FIG. 24 is for one embodiment, as an example, for tip.

FIGS. 22A, 22B, and 22C show views of the tip, with spiral tip 162, for one embodiment, with 3D views and a cross section from half/middle, for one-fin spiral configuration. FIG. 23 shows a view of the tip, with spiral tip 164, for one embodiment, with 3D view, for one-fin spiral configuration. FIG. 24 shows a view of the tip, with spiral tip 166, for one embodiment, with 3D view, for one-fin spiral configuration.

Figure 25:
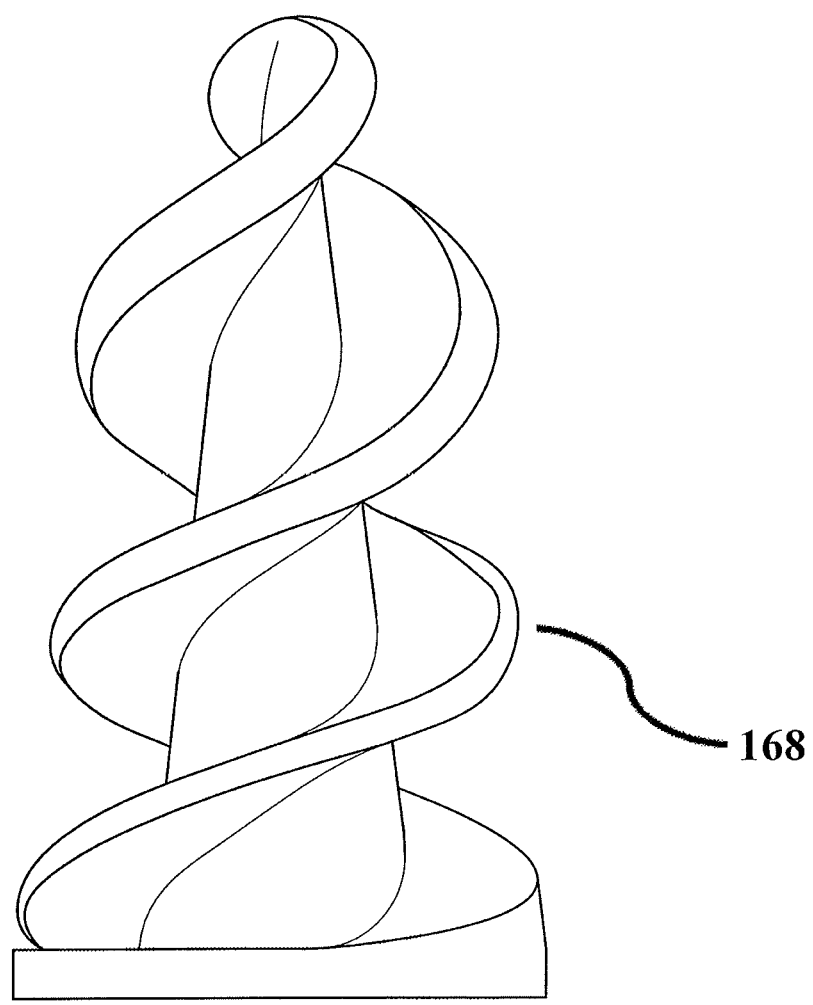
FIG. 25 is for one embodiment, as an example, for tip.
Figure 26:
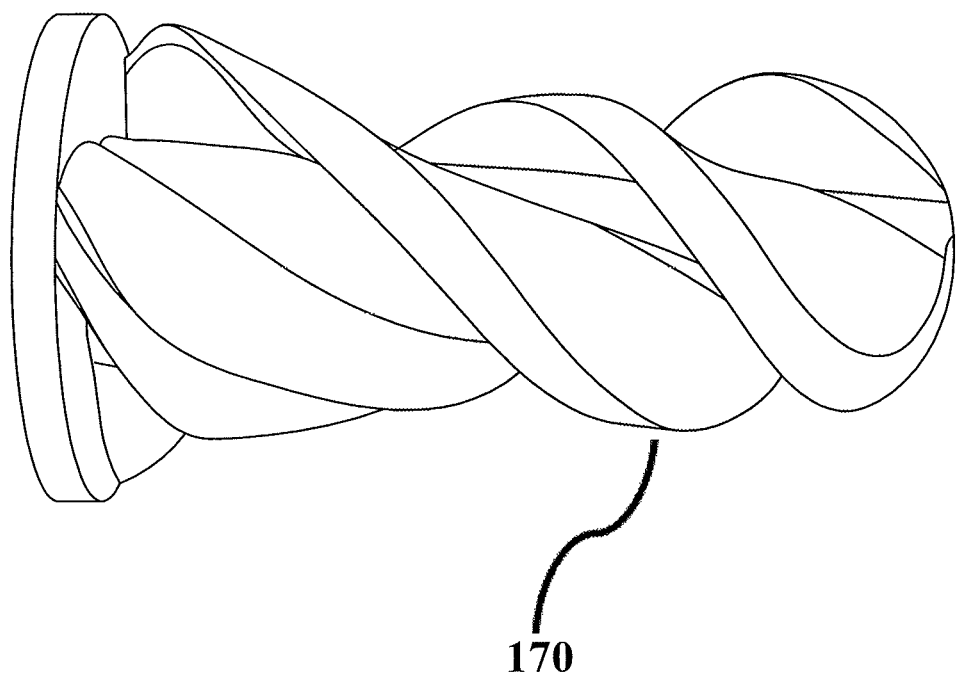
FIG. 26 is for one embodiment, as an example, for tip.

FIG. 25 shows a view of the tip, with spiral tip 168, for one embodiment, with 3D view, for two-fin spiral configuration. FIG. 26 shows a view of the tip, with spiral tip 170, for one embodiment, with 3D view, for three-fin spiral configuration.

Figure 27:
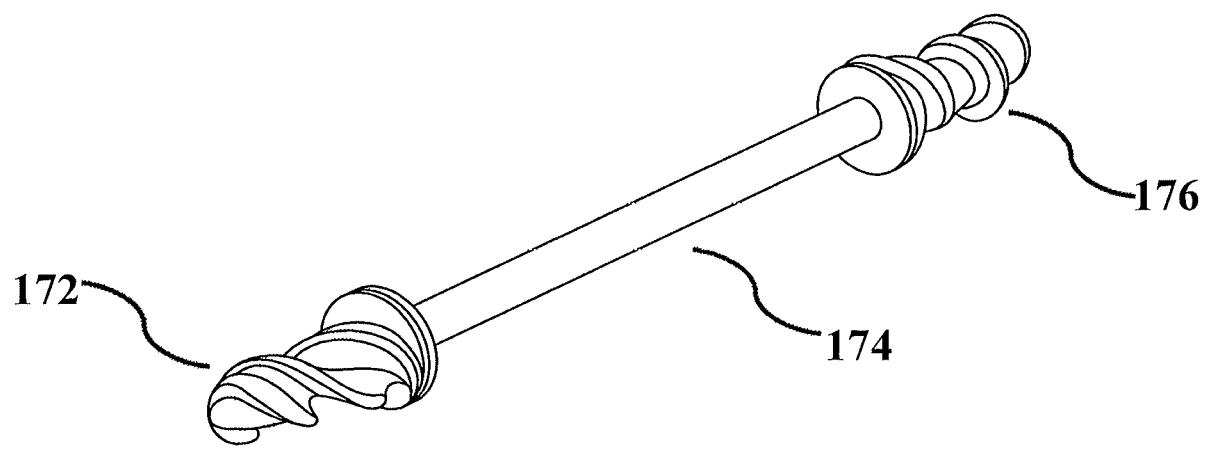
FIG. 27 is for one embodiment, as an example, for handle and tip.
Figure 28:
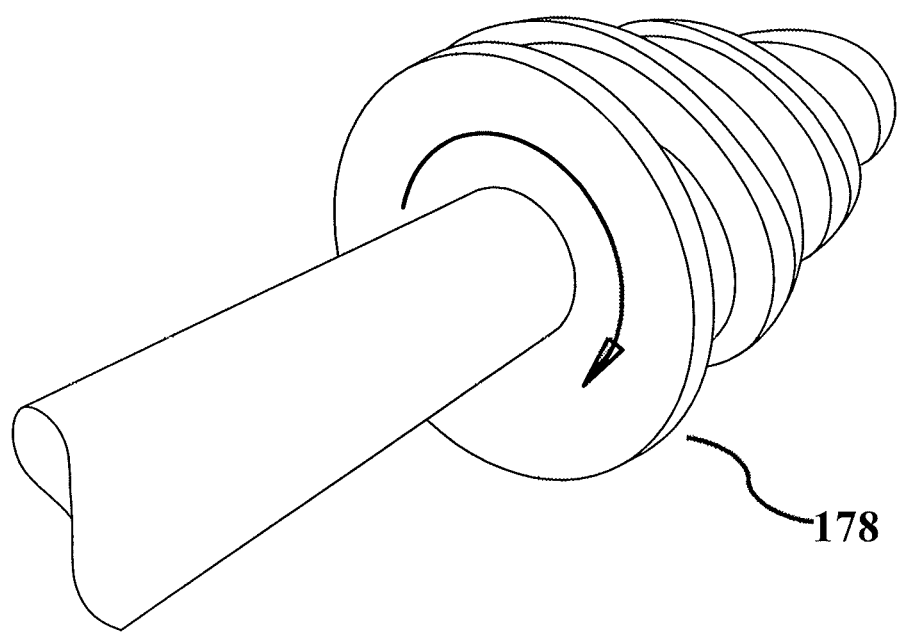
FIG. 28 is for one embodiment, as an example, for handle and tip.
Figure 29:
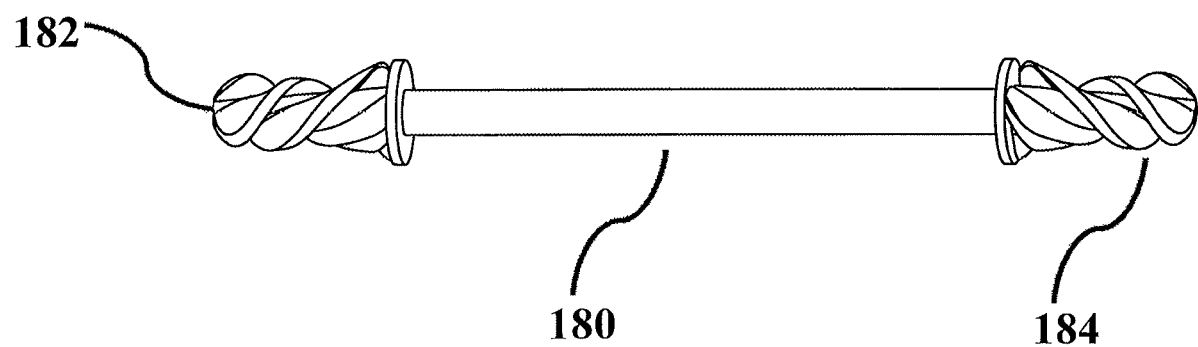
FIG. 29 is for one embodiment, as an example, for handle and tip.
Figure 31A:
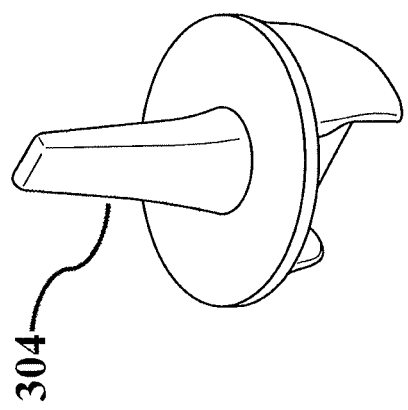
FIG. 31A is for one embodiment, as an example, for tip.
Figure 31C:
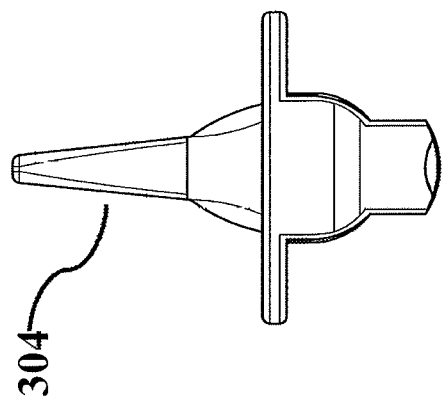
FIG. 31C is for one embodiment, as an example, for tip.
Figure 31B:
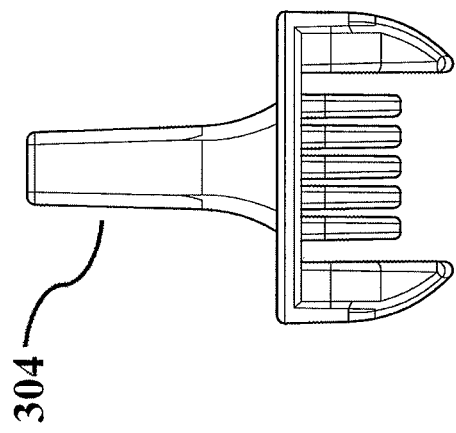
FIG. 31B is for one embodiment, as an example, for tip.
Figure 31E:
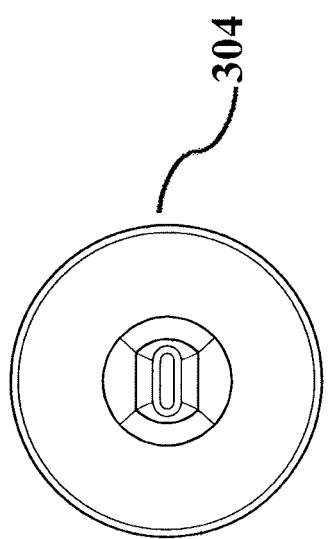
FIG. 31E is for one embodiment, as an example, for tip.
Figure 31D:
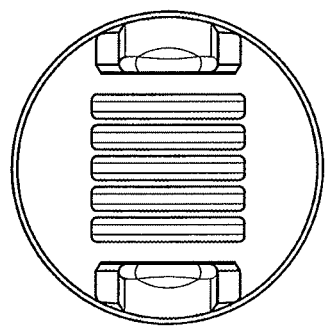
FIG. 31D is for one embodiment, as an example, for tip.

FIG. 27 shows a view of the 2 tips at 2 ends of a handle or body 174, with spiral tips 174, 176, for one embodiment, with 3D view. FIG. 28 shows a view of the spiral tip 178, for one embodiment, with 3D view. FIG. 29 shows a view of the 2 tips at 2 ends of a handle or body 180, with spiral tips 182, 184, for one embodiment, with 3D view.

As shown above, we can have N-fin spiral configuration, but after or above N=3, it may not be any more efficient in action as the lower number fin situations on the spiral tip, for the removal of ear wax. So, for most cases, in one embodiment, we use 2-fin and 3-fin configurations. One-fin models are very simple in design and still do the job very well.

As shown above, in figures, for one embodiment, we have rib shape or tubs or multiple pins or array of small bars or brush shape or comb shape, for the tip and/or body, to lock into each other, with slit or opening on the other side to engage the other side, to lock in and attach with each other, as one unit. The locking is done by pushing these two parts toward each other, to snap into a locked position. To release, the fingers push on the locked parts, to push in, and pull apart the parts simultaneously, to get the parts separated from each other. So, we can do the snap off by fingers, to separate them (tip separated from the body).

For one embodiment, we have touch free tip replacement, with clean tip or sterilized tip, without touching with fingers to avoid contamination the tip. For one embodiment, we have locking system for the tip and body. For one embodiment, we can have any material for the body or handle, e.g., metal, alloy, plastic, rubber, elastic, wood, polymer, glass, or the like. For one embodiment, we have bowl shaped or spoon shaped tip for scooping the ear wax easier and more efficiently, and avoid sharp edges on tip in the ear canal for possible injury.

For one embodiment, we have tip made of open cell foam, moist absorbent, regular foam, sponge, cotton, clothing, soft tissue, towel, Q-tip material, wool, silk, nylon, acrylic, petroleum based material, synthetic material, porous material for absorbing moisture and liquid, dry fabric, filter material, coarse material, bumpy surface material, or the like.

For one embodiment, we have container or box or enclosure or tube or filler or space or storage or liquid holder for liquid or fluid for cleaning ear, e.g., wash, anti-bacteria, dissolve wax, soften wax, rinse, dry, or the like, through for example, the tip or holes or syringe shape or the like. For one embodiment, we have disposable tip. For one embodiment, we have the pressure from the back side, instead of the handle, to remove the tip.

For one embodiment, we have liquid stored in the end of the body or the whole body. For one embodiment, we have pushing mechanism to push the liquid out to clean the ear. For one embodiment, we have spoon or scoop shape at the head of the tip, to better take out the wax, or use a wide-curved surface for that purpose. For one embodiment, we have syringe operation with handle for holding the liquid, to load and unload. For one embodiment, we have piston to load and unload liquid.

For one embodiment, we have cap like grooves to rotate the tip into the body similar to the screw action, to lock that in, to attach to the body or handle. For one embodiment, we have syringe action to suck the liquid and store and then push the piston to eject the liquid for use. For one embodiment, we have core piece attached to the tip, with holes in the core piece, for different positions and directions, dispensing liquid into the ear.

For one embodiment, we have syringe bulb as elastic sphere for use of liquid and storage into the container within body. For one embodiment, we have 2 holes on core piece at one end to engage with the tip. For one embodiment, we have variations on holes (number and shapes and patterns) on core piece. For one embodiment, we have syringe bulb for suction action and function at the end of the handle, similar to eye dripper device. For one embodiment, we have one piece tab or tongue to go into groove or opening for better locking purpose and longevity of the tab or tongue. For one embodiment, we have elastic or flexible material for tip to have a soft tip for better operation.

For one embodiment, we have container for liquid as glass, metal, plastic, wood, fiber, or the like. For one embodiment, we have o-ring or copper ring or plastic ring or elastic ring or band or the like, to avoid leaking from the container or syringe sides or cylinder sides, inside the handle or body, for proper operation.

Figure 33:
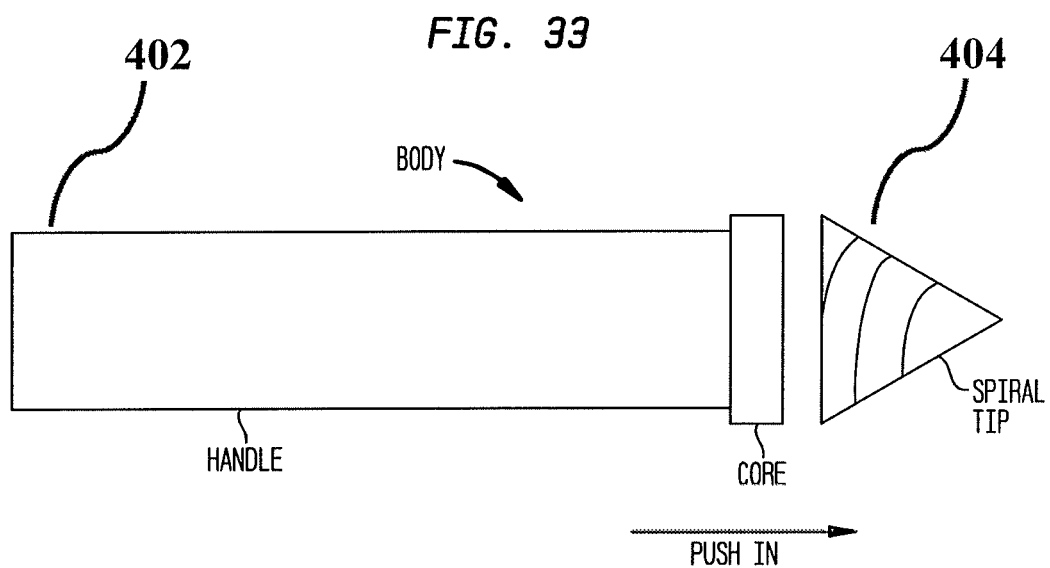
FIG. 33 is for one embodiment, as an example, for handle and tip.
Figure 34:
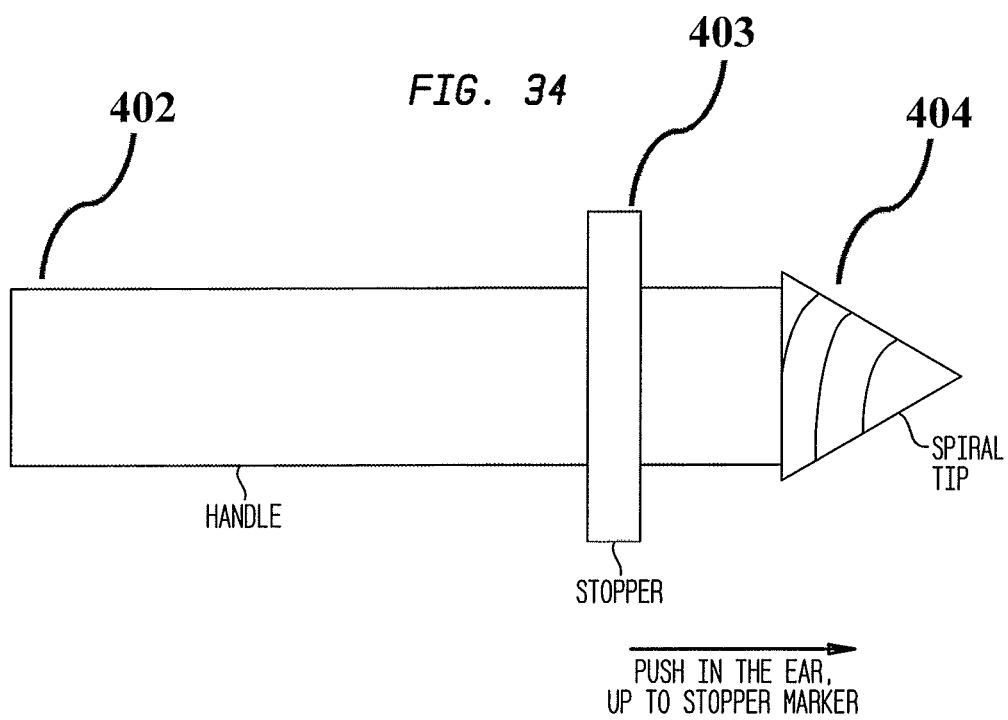
FIG. 34 is for one embodiment, as an example, for handle and tip, with stopper.
Figure 35:
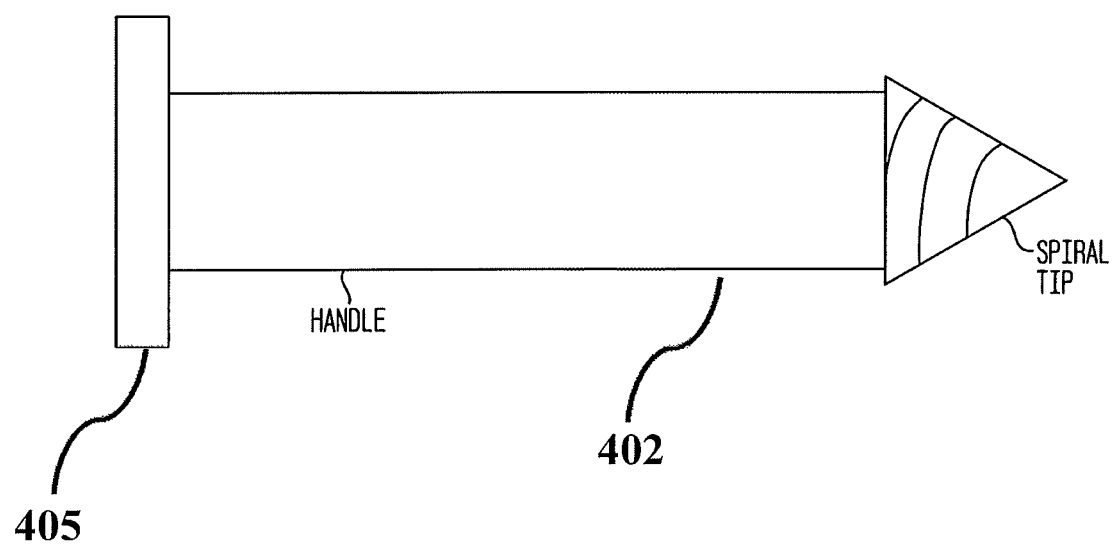
FIG. 35 is for one embodiment, as an example, for handle with extra grip place.
Figure 36:
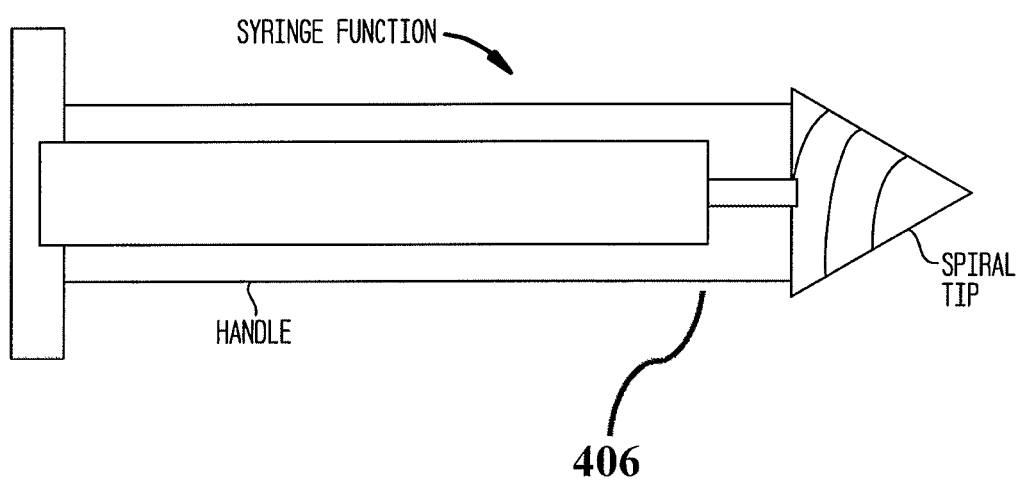
FIG. 36 is for one embodiment, as an example, for handle with syringe function.
Figure 37:
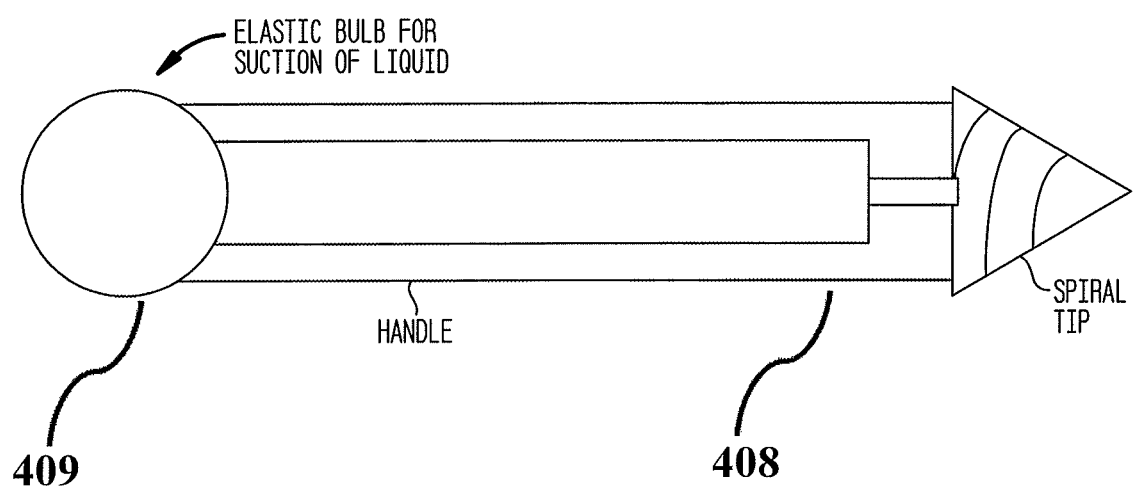
FIG. 37 is for one embodiment, as an example, for handle with elastic bulb for suction.

FIG. 33 is for one embodiment, as an example, for handle 402 and tip 404. FIG. 34 is for one embodiment, as an example, for handle 402 and tip 404, with stopper 403. FIG. 35 is for one embodiment, as an example, for handle 402 with extra grip place 405. FIG. 36 is for one embodiment, as an example, for handle 406 with syringe function. FIG. 37 is for one embodiment, as an example, for handle 408 with elastic bulb 409 for suction.

Figure 38:
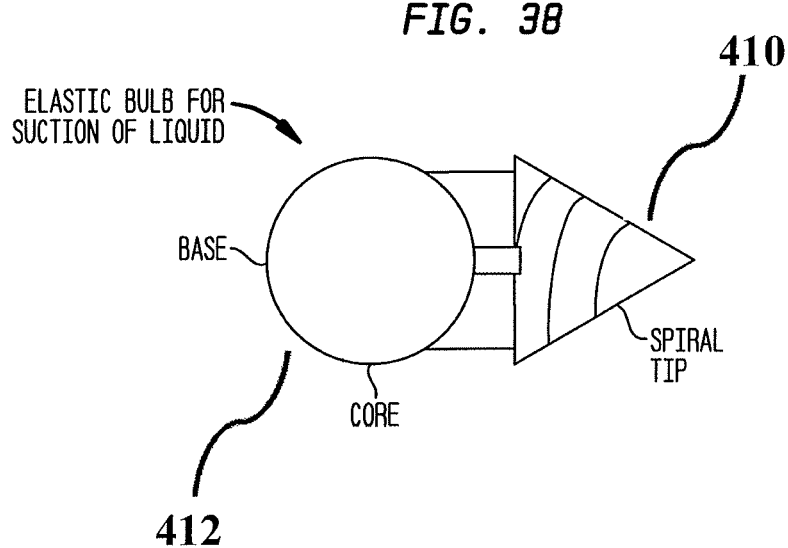
FIG. 38 is for one embodiment, as an example, for core/base and tip.
Figure 39:
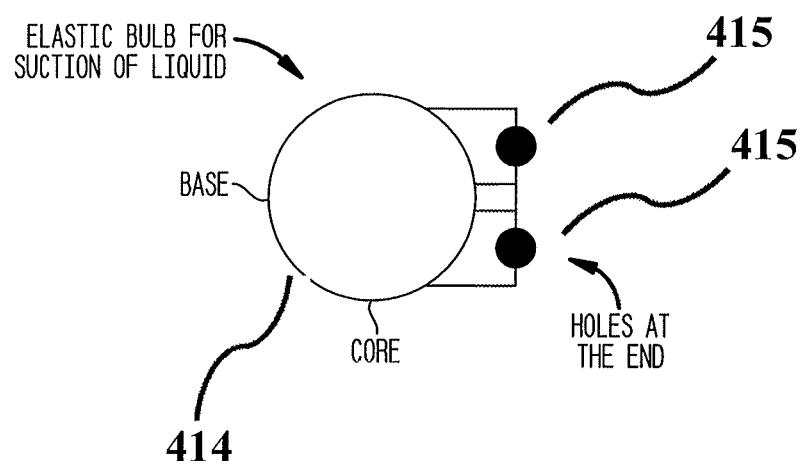
FIG. 39 is for one embodiment, as an example, for base with holes.
Figure 40:
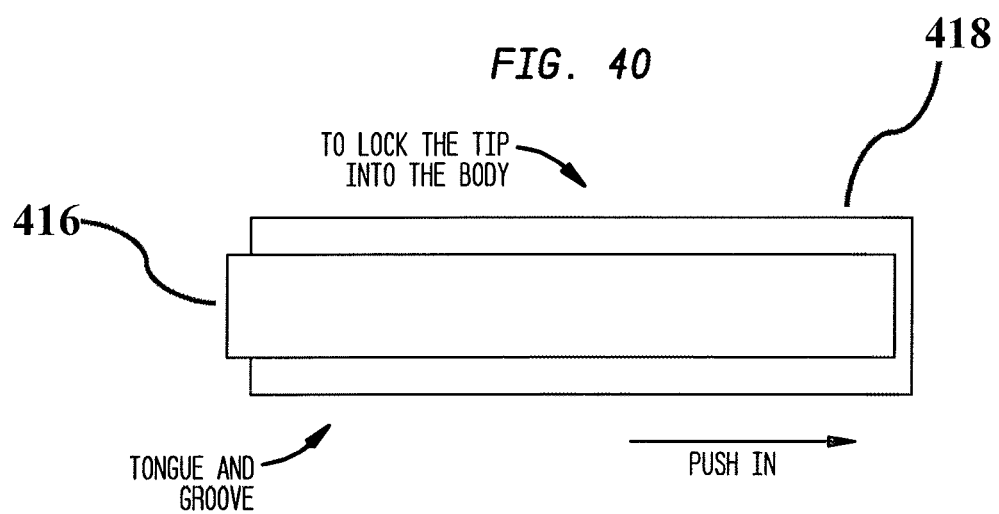
FIG. 40 is for one embodiment, as an example, for tongue and groove to lock the tip into the body, as one piece.
Figure 41:
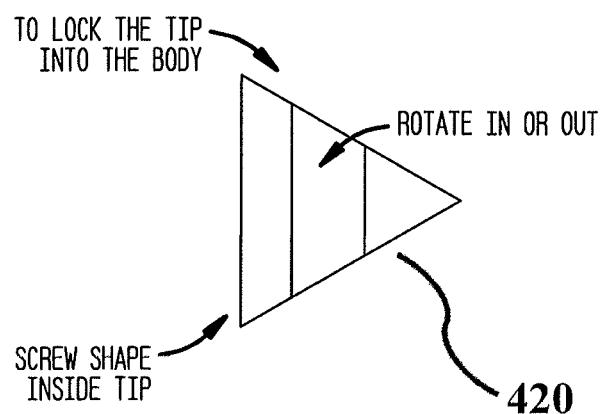
FIG. 41 is for one embodiment, as an example, for screw action inside the tip, to lock into the body.
Figure 42:
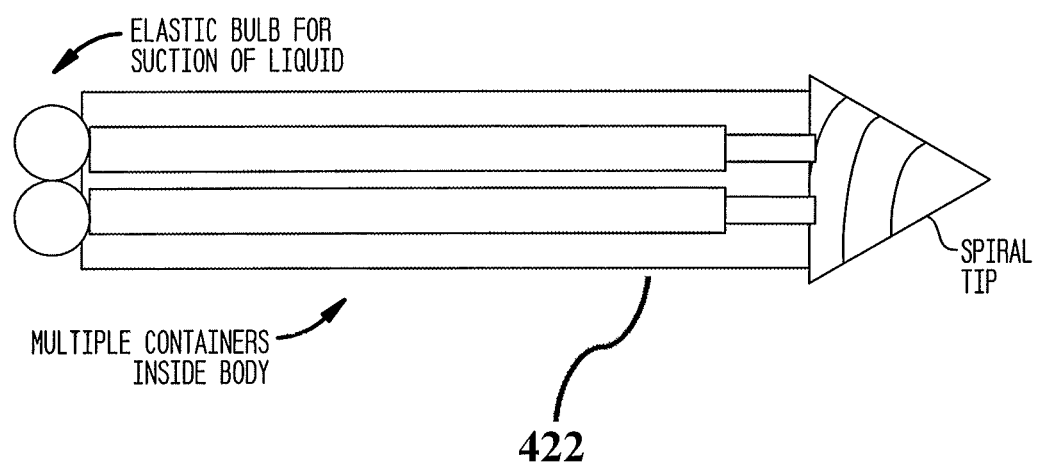
FIG. 42 is for one embodiment, as an example, for multiple containers (2 or more) inside body or handle.

FIG. 38 is for one embodiment, as an example, for core/base 412 and tip 410. FIG. 39 is for one embodiment, as an example, for base 414 with holes 415. FIG. 40 is for one embodiment, as an example, for tongue and groove to lock the tip 416 into the body 418, as one piece. FIG. 41 is for one embodiment, as an example, for screw action inside the tip 420, to lock into the body. FIG. 42 is for one embodiment, as an example, for multiple containers (2 or more) inside body or handle 422.

Figure 43:
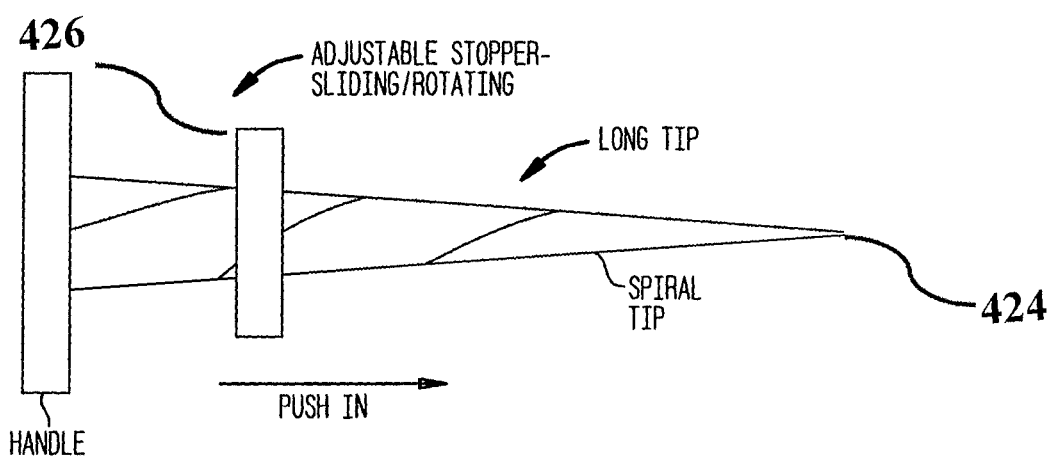
FIG. 43 is for one embodiment, as an example, for long tip with stopper.
Figure 44:
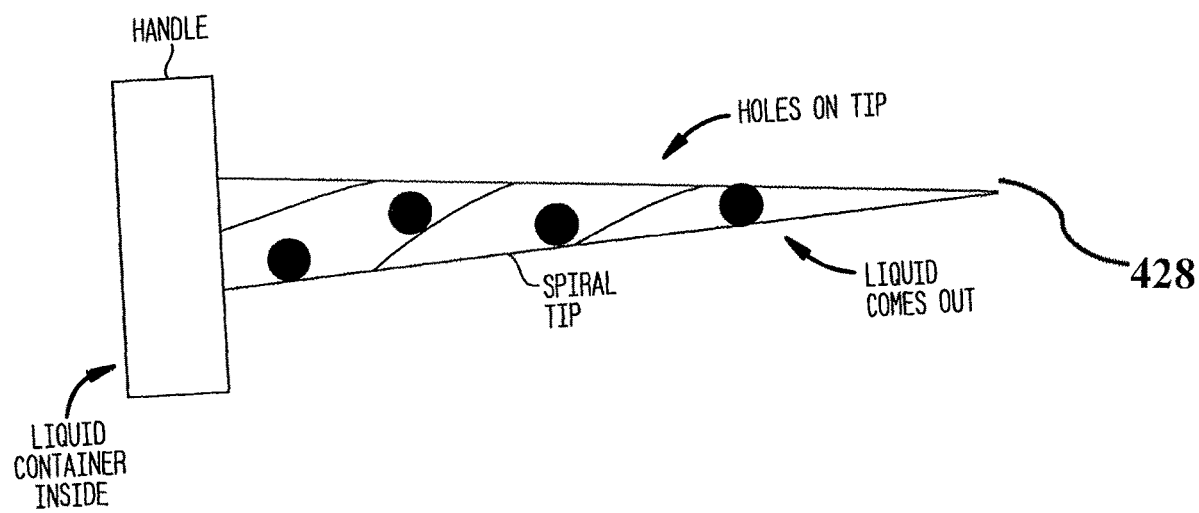
FIG. 44 is for one embodiment, as an example, for tip with holes.
Figure 45:
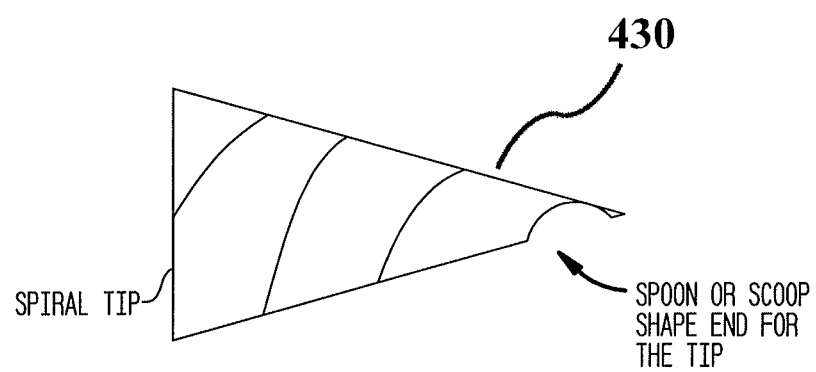
FIG. 45 is for one embodiment, as an example, for tip with the end acting as spoon or scoop, with curved wide area or surface.

FIG. 43 is for one embodiment, as an example, for long tip 424 with stopper 426. FIG. 44 is for one embodiment, as an example, for tip 428 with holes. FIG. 45 is for one embodiment, as an example, for tip 430 with the end acting as spoon or scoop, with curved wide area or surface.

Any variations of the above teaching are also intended to be covered by this patent application.

The invention claimed is:

1. An ear cleaning apparatus comprising:
   a spiral-shaped head;
   a locking mechanism coupled to the spiral-shaped head, the locking mechanism including a center protrusion and a pair of longitudinally extending locking tabs; and
   a handle including a receiving portion configured to receive the locking mechanism to releasably couple the spiral-shaped head to the handle,
   wherein the center protrusion includes a plurality of ribs.

2. The ear cleaning apparatus of claim 1, wherein the spiral-shaped head includes a soft material.

3. The ear cleaning apparatus of claim 1, wherein the spiral-shaped head includes a foam material.

4. The ear cleaning apparatus of claim 1, wherein the spiral-shaped head includes a plastic material.

5. The ear cleaning apparatus of claim 1, wherein the spiral-shaped head is porous.

6. The ear cleaning apparatus of claim 1, wherein the locking mechanism is configured such that the spiral-shaped head is removable from the receiving portion via a pressure applied to one of the pair of locking tabs.

7. The ear cleaning apparatus of claim 1, wherein the spiral-shaped head and locking mechanism are configured to be removably coupled and decoupled from the handle without touching the spiral-shaped head.

8. The ear cleaning apparatus of claim 1, wherein the spiral-shaped head is disposable.

9. The ear cleaning apparatus of claim 1, wherein the locking mechanism is disposable.

10. The ear cleaning apparatus of claim 1, wherein the ear cleaning apparatus includes a stopper configured to prevent excessive insertion of the ear cleaning apparatus into an ear canal.

11. The ear cleaning apparatus of claim 10, wherein the handle includes the stopper.

12. The ear cleaning apparatus of claim 10, wherein the stopper is adjustable.

13. The ear cleaning apparatus of claim 10, wherein the spiral-shaped head includes a tapered shape, and the tapered shape acts as the stopper.

14. The ear cleaning apparatus of claim 1, wherein the handle includes at least one container for liquid.

15. The ear cleaning apparatus of claim 1, wherein the head includes at least one container for liquid.

16. The ear cleaning apparatus of claim 1, wherein the ear cleaning apparatus includes a syringe.

17. The ear cleaning apparatus of claim 1, wherein the spiral-shaped head includes a spoon-shaped feature disposed at a distal end of the spiral-shaped head.

18. An ear cleaning apparatus comprising:
a spiral-shaped head;
a locking mechanism coupled to the spiral-shaped head, the locking mechanism including a center protrusion and a pair of longitudinally extending locking tabs; and
a handle including a receiving portion configured to receive the locking mechanism to releasably couple the spiral-shaped head to the handle,
wherein the spiral-shaped head includes a spoon-shaped feature disposed at a distal end of the spiral-shaped head.

19. The ear cleaning apparatus of claim 18, wherein the center protrusion includes a plurality of ribs.

* * * * *